United States Patent
Yi et al.

(10) Patent No.: US 11,014,890 B2
(45) Date of Patent: May 25, 2021

(54) FORMS OF (R)-N-(4-CHLOROPHENYL)-2-(CIS-4-(6-FLUOROQUINOLIN-4-YL)CYCLOHEXYL)PROPANAMIDE

(71) Applicant: SHENZHEN RENTAI PHARMATECH LTD, Guangdong (CN)

(72) Inventors: Dongxu Yi, Shenzhen (CN); Guobin Ren, Shenzhen (CN); Jian Ma, Shenzhen (CN); Shuhao Wen, Shenzhen (CN); Peiyu Zhang, Shenzhen (CN); Yang Liu, Shenzhen (CN); Xuekun Shi, Shenzhen (CN); Jiajun Huang, Shenzhen (CN); Yanqi Zhang, Shenzhen (CN); Shigang Ruan, Shenzhen (CN); Mingjun Yang, Shenzhen (CN); Guangxu Sun, Shenzhen (CN)

(73) Assignee: SHENZHEN RENTAI PHARMATECH LTD, Guangdong (CN)

( * ) Notice: Subject to any disclaimer, the term of this patent is extended or adjusted under 35 U.S.C. 154(b) by 1 day.

(21) Appl. No.: 16/402,314

(22) Filed: May 3, 2019

(65) Prior Publication Data
US 2020/0002282 A1  Jan. 2, 2020

Related U.S. Application Data

(63) Continuation of application No. PCT/CN2018/093034, filed on Jun. 27, 2018.

(51) Int. Cl.
*C07D 215/18* (2006.01)
(52) U.S. Cl.
CPC ........ *C07D 215/18* (2013.01); *C07B 2200/13* (2013.01)
(58) Field of Classification Search
CPC .................................................... C07D 215/18
USPC ......................................... 546/180; 514/311
See application file for complete search history.

(56) References Cited

U.S. PATENT DOCUMENTS

| 6,627,646 | B2 * | 9/2003 | Bakale .................... A61P 37/08 514/322 |
| 9,463,972 | B2 | 10/2016 | Hitzelberger et al. |
| 2019/0002472 | A1 | 1/2019 | Beck et al. |
| 2020/0115342 | A1 * | 4/2020 | Powers .............. A61K 31/4353 |

FOREIGN PATENT DOCUMENTS

| CA | 2964290 | 5/2016 |
| CN | 107427499 A | 12/2017 |
| CN | 111093651 A | 5/2020 |

OTHER PUBLICATIONS

Guillory (in Brittain ed.). "Polymorphism in Pharmaceutical Solids", NY:Marcel Dekker, Inc., 235-238. (Year: 1999).*
CMU Pharmaceutical polymorphism, internet p. 1-3 printout Apr. 3, 2008. (Year: 2002).*
Singhal et al., "Drug Polymorphism, etc.," Advanced Drug Delivery reviews 56, p. 335-347. (Year: 2004).*
Concise Encyclopedia Chemistry, NY: Walter de Gruyter, 872-873. (Year: 1993).*
Jain et al., Polymorphism in Pharmacy, Indian Drugs, 23(6) 315-329. (Year: 1979).*
Muzaffar et al., "Polymorphism and Drug, etc.," J of Pharm. (Lahore), 1(1), 59-66. (Year: 1979).*
U.S. Pharmacopia #23, National Formulary #18, 1843-1844. (Year: 1995).*
Doelker, english translation of S.T.P. Pratiques, 9(5), 399-409, pp. 1-33. (Year: 1999).*
Doelker, english translation of Ann. Pharm. Fr., 60: 161-176, pp. 1-39. (Year: 2002).*
Taday et al, "Using Terahertz, etc.," J of Pharm. Sci., 92(4), 831-838. (Year: 2003).*
Otuska et al., "Effect of Polymorphic, etc.," Chem. Pharm. Bull., 47(6) 852-856. (Year: 1999).*
International Search Report & Written Opinion, PCT/CN2018/093034, dated Dec. 18, 2018, 9 pages.
Peter L. Toogood Small Molecule Immune-oncology Therapeutic Agents Bioorganic & Medicinal Chemistry Letters, Dec. 20, 2017, ISSN: 0960-894X, 11 pages.
Clinical Cancer Research, Prognostic Value of Indoleamine 2, 3-dioxygenase expression in colorectal cancer: effect on tumor-infiltrating T cells; Gerald Brandcher, Alexander Perathoner, Ruth Ladurner, et al.; Feb. 17, 2006; 10 pages.
Yang LV et al.; Polymorphic Drugs; People's Medical Publishing House; Oct. 2009; 7 pages.
J.Am.Chem.Soc 2018, 140, page No.'s 14538-14541, Journal of the American Chemical Society "Mapping the Binding Trajectory of a Suicide Inhibitor in Human Indoleamine 2,3-Dioxygenase 1".
"Notification of First Office Action", Application No. 2018800015412; dated Jan. 15, 2021; pp. 1-7.

* cited by examiner

*Primary Examiner* — Patricia L Morris
(74) *Attorney, Agent, or Firm* — Taft Stettinius & Hollister LLP; Stephen F. Rost

(57) ABSTRACT

Forms B and C of (R)—N-(4-chlorophenyl)-2-(cis-4-(6-fluoroquinolin-4-yl)cyclohexyl)propanamide are stable under the conditions of light, high temperature and high humidity.

2 Claims, 22 Drawing Sheets

FORMS OF (R)-N-(4-CHLOROPHENYL)-2-(CIS-4-(6-FLUOROQUINOLIN-4-YL)CYCLOHEXYL)PROPANAMIDE

RELATED APPLICATIONS

This application is a continuation of International Application PCT/CN2018/093034, filed Jun. 27, 2018, the disclosure of which is hereby incorporated by reference in its entirety.

TECHNICAL FIELD

The present invention relates to the technical field of crystal form preparation, in particular to forms of (R)—N-(4-chlorophenyl)-2-(cis-4-(6-fluoroquinolin-4-yl)cyclohexyl)propanamide and preparation methods thereof, and a pharmaceutical composition prepared therefrom.

BACKGROUND

Indoleamine 2,3-dioxygenase (IDO; also known as IDO1) is an IFN-γ target gene that plays a role in immune regulation. IDO is an oxidoreductase and is one of two enzymes that catalyze the first and rate-limiting step in the conversion of tryptophan to N-formyl-kynurenine. IDO plays a major role in immune regulation and its immunosuppressive function is shown in several ways. Importantly, IDO regulates immunity at the T-cell level and there is a relationship between IDO and cytokine production. In addition, tumors frequently manipulate immune function by up-regulating IDO. Thus, modulation of IDO can have therapeutic effects on a variety of diseases, symptoms and conditions.

There is a pathophysiological link between IDO and cancer. The destruction of immune homeostasis is closely related to tumor growth and development, and the production of IDO in the tumor microenvironment seems to help tumor growth and tumor metastasis. In addition, increased levels of IDO activity are associated with a variety of different tumors (Brandacher, G. et al, Clin. Cancer Res., 12(4): 1144-1151 (Feb. 15, 2006)). In addition to cancer, IDO has been particularly implicated in immunosuppression, chronic infections, and autoimmune diseases or symptoms (e.g., rheumatoid arthritis). Therefore, inhibition of tryptophan degradation by inhibiting IDO activity has great therapeutic value. Furthermore, inhibitors of IDO can be used to enhance T cell activation when T cells are suppressed by pregnancy, malignant diseases or viruses such as HIV. In addition, IDO inhibitors can also be used to treat patients with neurological or neuropsychiatric diseases or symptoms such as depression.

In view of the role of indoleamine 2,3-dioxygenase in a range of different diseases, symptoms and conditions and the efficacy of current IDO inhibitors, U.S. Pat. No. 9,643,972B2 discloses new IDO modulators and related compositions thereof (R)—N-(4-chlorophenyl)-2-(cis-4-(6-fluoroquinolin-4-yl)cyclohexyl)propanamide disclosed in this patent document has the following structural formula,

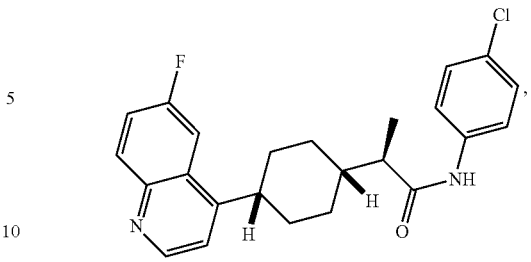

which is an amorphous structure. Chinese researchers have found that crystal structures are still not available using a variety of known crystal form screening methods, while amorphous substances are relatively poorly stable under a variety of environmental conditions. Thereby, the active substance, pharmaceutical formulation or pharmaceutical composition has poor stability, especially poor hygroscopic stability. It is well known that the absorption of moisture will reduce the content of the pharmaceutically active substance which is increased in weight by taking up moisture. The pharmaceutical composition which tends to absorb moisture needs to avoid moisture during storage, and the addition of a desiccant or storage in a moisture-proof environment undoubtedly increases the storage cost of the drug. Thus, it can be seen that the preparation of a substance having good hygroscopic stability is of great significance both for storage and for maintaining the content of the pharmaceutically active substance.

SUMMARY

Therefore, the present invention aims to overcome the defect that only the amorphous product of (R)—N-(4-chlorophenyl)-2-(cis-4-(6-fluoroquinolin-4-yl)cyclohexyl)propanamide can be obtained in the prior art, and provides new forms of (R)—N-(4-chlorophenyl)-2-(cis-4-(6-fluoroquinolin-4-yl)cyclohexyl)propanamide. The present invention provides crystalline (R)—N-(4-chlorophenyl)-2-(cis-4-(6-fluoroquinolin-4-yl)cyclohexyl)propanamide.

The present invention further provides a crystalline monohydrate (R)—N-(4-chlorophenyl)-2-(cis-4-(6-fluoroquinolin-4-yl)cyclohexyl)propanamide.

The present invention further provides a monohydrate of (R)—N-(4-chlorophenyl)-2-(cis-4-(6-fluoroquinolin-4-yl)cyclohexyl)propanamide.

The DSC onset melting temperature of any of the above-mentioned compounds is between 100° C. and 101° C.

The weight loss of any of the above-mentioned compounds is 4% when heated to 150° C. The X-ray powder diffraction pattern of any of the above-mentioned compounds has characteristic peaks when 2θ is 7.0, 9.5, 12.4 and 13.7.

The present invention further provides Form B of the crystalline monohydrate (R)—N-(4-chlorophenyl)-2-(cis-4-(6-fluoroquinolin-4-yl)cyclohexyl)propanamide.

The X-ray powder diffraction pattern of Form B has two characteristic peaks when 2θ is between 7.0 and 12.0.

The X-ray powder diffraction pattern of Form B has a characteristic peak when 2θ is 7.0.

The X-ray powder diffraction pattern of Form B has a characteristic peak when 2θ is 9.5.

The X-ray powder diffraction pattern of Form B has a characteristic peak when 2θ is 12.4.

The X-ray powder diffraction pattern of Form B has a characteristic peak when 2θ is 13.7.

Any of the above-mentioned compounds has a monoclinic crystal system.

The unit cell volume of any of the above-mentioned compounds is between 2130 Å$^3$ and 2330 Å$^3$.

The space group of any of the above-mentioned compounds is C2.

The present invention provides Form B of (R)—N-(4-chlorophenyl)-2-(cis-4-(6-fluoroquinolin-4-yl)cyclohexyl)propanamide, wherein the X-ray powder diffraction pattern mainly has the following characteristic peaks,

| Angle 2θ |
| --- |
| 6.985 ± 0.2 |
| 9.447 ± 0.2 |
| 12.398 ± 0.2 |
| 13.677 ± 0.2 |
| 17.171 ± 0.2 |
| 17.644 ± 0.2 |
| 18.985 ± 0.2 |
| 20.142 ± 0.2 |
| 21.118 ± 0.2 |
| 21.62 ± 0.2 |
| 22.199 ± 0.2 |
| 24.173 ± 0.2 |
| 24.915 ± 0.2 |
| 26.828 ± 0.2 |
| 28.682 ± 0.2 |
| 30.418 ± 0.2 |
| 31.46 ± 0.2. |

Form B of (R)—N-(4-chlorophenyl)-2-(cis-4-(6-fluoroquinolin-4-yl)cyclohexyl)propanamide of the present invention, wherein Form B is a monoclinic crystal system, the space group is C2, the unit cell dimensions are a=25.358(9) Å, b=10.016(3) Å, c=8.788(3) Å, α=90°, =91.57(2°), γ=90° and Z=4, and the unit cell volume is 2231.2(14)Å$^3$.

Form B of (R)—N-(4-chlorophenyl)-2-(cis-4-(6-fluoroquinolin-4-yl)cyclohexyl)propanamide of the present invention, wherein the DSC pattern has an endothermic peak at 109±3° C. In a specific implementation of the present invention, the DSC pattern of Form B has an endothermic peak at 109.93° C.

Form B of (R)—N-(4-chlorophenyl)-2-(cis-4-(6-fluoroquinolin-4-yl)cyclohexyl)propanamide of the present invention, wherein in a TGA pattern, the weight loss is between 4% and 4.2%. In a specific implementation of the present invention, the weight loss of Form B in the TGA pattern is 4.047%.

The present invention further provides a method for preparing any above-mentioned Form C of (R)—N-(4-chlorophenyl)-2-(cis-4-(6-fluoroquinolin-4-yl)cyclohexyl)propanamide, comprising: adding amorphous (R)—N-(4-chlorophenyl)-2-(cis-4-(6-fluoroquinolin-4-yl)cyclohexyl)propanamide to water, heating to 90° C., stirring, filtering to obtain a solidified solid, adding the solidified solid to a surfactant-containing organic solution, and performing crystallization. Preferably, the ratio of amorphous (R)—N-(4-chlorophenyl)-2-(cis-4-(6-fluoroquinolin-4-yl)cyclohexyl)propanamide to water is 6 mg/ml. The organic solution is a methanol aqueous solution, wherein the volume ratio of methanol to water is (8-5):1; and the surfactant is sodium dodecylbenzenesulfonate, and the volume ratio of the sodium dodecyl benzene sulfonate to the water in the methanol aqueous solution is 1:1000. The method for growing the single crystal of Form B of (R)—N-(4-chlorophenyl)-2-(cis-4-(6-fluoroquinolin-4-yl)cyclohexyl)propanamide of the present invention, wherein the filtered solidified solid is pulverized and added to a solution of methanol, water and sodium dodecylbenzenesulfonate, the mixture is stirred and filtered, and the filtered product is washed and vacuum-dried to obtain the crystal.

The present invention further provides a method for preparing Form B by induced crystallization using Form B of (R)—N-(4-chlorophenyl)-2-(cis-4-(6-fluoroquinolin-4-yl)cyclohexyl)propanamide as a seed crystal, comprising: adding the amorphous (R)—N-(4-chlorophenyl)-2-(cis-4-(6-fluoroquinolin-4-yl)cyclohexyl)propanamide to an aqueous solution of a second organic solvent, adding the crystal obtained by any of the above-mentioned preparation methods, shaking the mixture at 50° C. for 12 h, filtering, washing, and vacuum drying. Preferably, the second organic solvent is tetrahydrofuran, acetone or acetonitrile. The ratio of the second organic solvent to water is 6 mg/ml. The ratio of the amorphous (R)—N-(4-chlorophenyl)-2-(cis-4-(6-fluoroquinolin-4-yl)cyclohexyl)propanamide to the aqueous solution of the second organic solvent is 6 mg/ml.

The present invention further provides a method for growing a single crystal of Form B of (R)—N-(4-chlorophenyl)-2-(cis-4-(6-fluoroquinolin-4-yl)cyclohexyl)propanamide, comprising: adding Form B obtained by any of the above-mentioned preparation methods to a methanol aqueous solution, performing ultrasonic treatment, putting the mixture in a 5° C. environment, arranging a micro hole having a hole diameter d 0.2 mm as a gas volatilization channel, and performing volatilization to obtain the single crystal of Form B. In an implementation of the present invention, the ultrasonic treatment is performed until a very small amount of solid is observed in the solution by naked eyes, the mixture is put in a 5° C. environment, a hole (d 0.2 mm) is punched out by a hole puncher after the sample bottle is sealed, and performing volatilization to obtain the single crystal of Form B. Preferably, the volume ratio of methanol to water is 1:4. The ultrasonic frequency is 40 KHz, and the power is 200 W. Data of the single crystal is shown in the table below.

Single Crystal Data

| | | |
| --- | --- | --- |
| Empirical formula | C24H26ClFN2O2 | |
| Formula weight | 428.92 | |
| Temperature | 201(2) K | |
| Wavelength | 1.54178 Å | |
| Crystal system | Monoclinic | |
| Space group | C2 | |
| Unit cell dimensions | a = 25.358(9) Å | □ = 90°. |
| | b = 10.016(3) Å | □ = 91.57(2)°. |
| | c = 8.788(3) Å | □ = 90°. |
| Volume | 2231.2(14) Å$^3$ | |
| Z | 4 | |

The present invention further provides Form C of (R)—N-(4-chlorophenyl)-2-(cis-4-(6-fluoroquinolin-4-yl)cyclohexyl)propanamide.

The X-ray powder diffraction pattern of Form C has characteristic peaks when 2θ is 8.5, 10.8, 11.8 or 14.8.

The DSC onset melting temperature of Form C is 101° C.

The present invention provides Form C of (R)—N-(4-chlorophenyl)-2-(cis-4-(6-fluoroquinolin-4-yl)cyclohexyl)propanamide, wherein the X-ray powder diffraction pattern mainly has the following characteristic peaks,

| Angle 2θ |
| --- |
| 8.465 ± 0.2 |
| 9.733 ± 0.2 |

-continued

| Angle 2θ |
| --- |
| 10.804 ± 0.2 |
| 11.818 ± 0.2 |
| 12.419 ± 0.2 |
| 13.656 ± 0.2 |
| 14.772 ± 0.2 |
| 15.926 ± 0.2 |
| 16.93 ± 0.2 |
| 17.247 ± 0.2 |
| 17.688 ± 0.2 |
| 18.203 ± 0.2 |
| 18.823 ± 0.2 |
| 19.066 ± 0.2 |
| 20.144 ± 0.2 |
| 21.16 ± 0.2 |
| 21.779 ± 0.2 |
| 22.26 ± 0.2 |
| 23.694 ± 0.2 |
| 24.234 ± 0.2 |
| 24.93 ± 0.2 |
| 27.703 ± 0.2 |
| 28.047 ± 0.2 |
| 28.743 ± 0.2 |
| 32.062 ± 0.2. |

Form C of (R)—N-(4-chlorophenyl)-2-(cis-4-(6-fluoroquinolin-4-yl)cyclohexyl)propanamide of the present invention, wherein the DSC pattern has endothermic peaks at 110±3° C. and 196±3° C. In a specific implementation of the present invention, Form C has endothermic peaks at 110.59° C. and 196.93° C.

Form C of (R)—N-(4-chlorophenyl)-2-(cis-4-(6-fluoroquinolin-4-yl)cyclohexyl)propanamide of the present invention, wherein in a TGA pattern, the weight loss is between 4% and 4.2%. In a specific implementation of the present invention, the weight loss of Form C is 4.098%.

The present invention further provides a method for preparing any above-mentioned Form C of (R)—N-(4-chlorophenyl)-2-(cis-4-(6-fluoroquinolin-4-yl)cyclohexyl)propanamide, comprising: adding amorphous (R)—N-(4-chlorophenyl)-2-(cis-4-(6-fluoroquinolin-4-yl)cyclohexyl)propanamide to water, heating to 90° C., stirring, filtering to obtain a solidified solid, adding the solidified solid to a surfactant-containing organic solution, and performing crystallization.

Form C of (R)—N-(4-chlorophenyl)-2-(cis-4-(6-fluoroquinolin-4-yl)cyclohexyl)propanamide provided by the present invention, wherein the ratio of amorphous (R)—N-(4-chlorophenyl)-2-(cis-4-(6-fluoroquinolin-4-yl)cyclohexyl)propanamide to water is 6 mg/ml.

The method for preparing Form C of (R)—N-(4-chlorophenyl)-2-(cis-4-(6-fluoroquinolin-4-yl)cyclohexyl)propanamide provided by the present invention, wherein the organic solution is a methanol aqueous solution, wherein the volume ratio of methanol to water is (8-5):1.

The method for preparing Form C of (R)—N-(4-chlorophenyl)-2-(cis-4-(6-fluoroquinolin-4-yl)cyclohexyl)propanamide provided by the present invention, wherein the filtered solidified solid is pulverized and added to a methanol aqueous solution, the mixture is stirred and filtered, and the filtered product is washed and vacuum-dried to obtain the crystal.

The method for preparing Form C of (R)—N-(4-chlorophenyl)-2-(cis-4-(6-fluoroquinolin-4-yl)cyclohexyl)propanamide provided by the present invention, wherein the temperature of the organic solution is 90° C.

The present invention further provides a pharmaceutical composition, comprising any of the above-mentioned crystals or crystalline monohydrates, and one or more pharmaceutically acceptable excipients.

The pharmaceutical composition, preferably, the formulation is orally available.

The pharmaceutical composition, preferably, the formulation is a tablet.

A method for treating a patient with cancer, comprising the step of administering to the patient a pharmaceutically effective dose of any of the pharmaceutical compositions. Wherein the cancer is melanoma, skin cancer, advanced cancer, non-small cell lung cancer or head and neck cancer, prostate cancer, colon cancer, rectal cancer, pancreatic cancer, cervical cancer, stomach cancer, endometrial cancer, brain cancer, liver cancer, bladder cancer, ovarian cancer, testicular cancer, head cancer, neck cancer, skin cancer, mesothelioma, white blood cell cancer, esophageal cancer, breast cancer, muscle cancer, connective tissue cancer, lung cancer, adrenal cancer, thyroid cancer, kidney cancer or bone cancer; or one or more of glioblastoma, mesothelioma, renal cell carcinoma, stomach cancer, sarcoma, choriocarcinoma, basal cell carcinoma or testicular seminoma.

The present invention gives for the first time Forms B and C of (R)—N-(4-chlorophenyl)-2-(cis-4-(6-fluoroquinolin-4-yl)cyclohexyl)propanamide, which are stable under light, high temperature and high humidity conditions. By performing single crystal growing on the obtained Form B, the single crystal simulated powder pattern coincides with the XRPD pattern of Form B, indicating Form B of the present invention is a single crystal.

DETAILED DESCRIPTION

Figure 1:
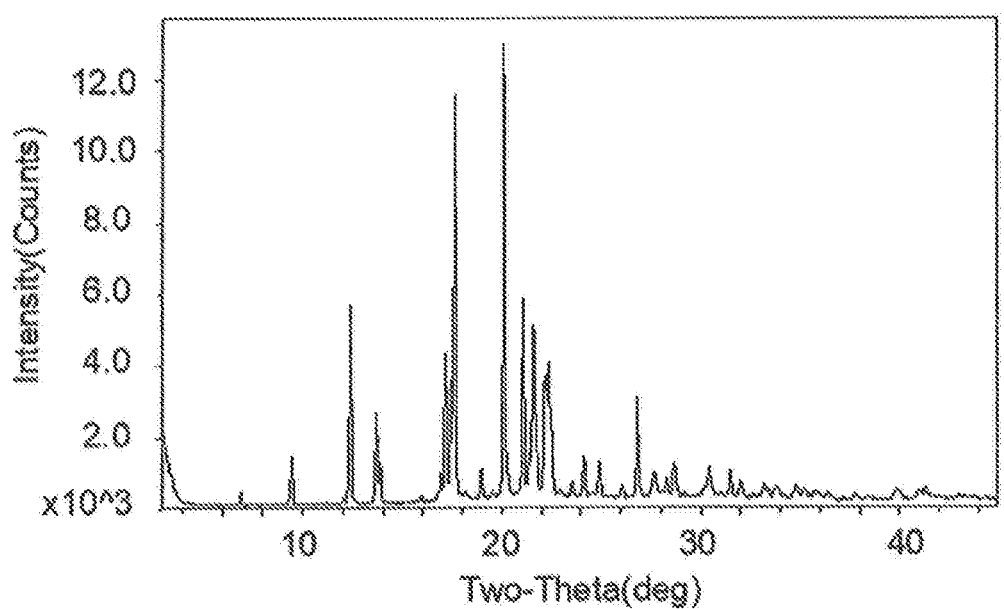
FIG. 1 is an X-ray powder diffraction pattern of Form B of Embodiment 1.

The amorphous active pharmaceutical ingredient in the following embodiments of the present invention refers to amorphous (R)—N-(4-chlorophenyl)-2-(cis-4-(6-fluoroquinolin-4-yl)cyclohexyl)propanamide. The present application provides a method for preparing the amorphous (R)—N-(4-chlorophenyl)-2-(cis-4-(6-fluoroquinolin-4-yl)cyclohexyl) propanamide for reference. It should be noted that the method for producing the amorphous active pharmaceutical ingredient is not limited to the method provided in the present application, and the amorphous active pharmaceutical ingredient obtained by any method in the prior art can be used to prepare the crystalline compound according to the method of the present application.

A reference method for preparing amorphous (R)—N-(4-chlorophenyl)-2-(cis-4-(6-fluoroquinolin-4-yl)cyclohexyl) propanamide is as follows:

To an oven-dried round bottom flask (Flask #1) was added 2-(4-(6-fluoroquinolin-4-yl)-cyclohexyl)acetic acid (1.0 eq) as a mixture of diastereomers. The flask was evacuated and backfilled with nitrogen and subsequently charged with THF (0.25 M) and triethylamine (2.0 eq). The resulting solution was cooled to −78° C. before the slow addition of pivaloyl chloride (1.25 eq) over 15 min. The reaction mixture was then stirred at 0° C. for 1 hour.

To a separate oven-dried round bottomed flask (Flask #2) was added (R)-2-phenyl-oxazolidinone (1.3 eq) and THF (0.25 M). This solution was cooled to −78° C. before the addition of n-BuLi (2.5M in hexanes, 1.3 eq). This reaction mixture was stirred at −78° C. for 15 minutes before being removed from the cold bath.

Flask #1 was then cooled back to −78° C. and the contents of Flask #2 were added to Flask #1 via cannula over the course of 15 minutes. After complete addition, the cold bath was removed and the reaction was stirred for 3 hours at 25° C. The reaction was quenched by addition of saturated ammonium chloride solution (100 mL) and subsequent extraction with ethyl acetate (100 mL×3). The combined organics were washed with brine, dried over sodium sulfate, filtered and concentrated. The crude residue was purified using silica gel chromatography to get cis product.

NaHMDS (2 M in THF, 1.2 eq) was added dropwise to 0.2M solution of the cis product (1.0 eq) in anhydrous tetrahydrofuran at −50° C. The solution was stirred for 10 min at −50° C. and then neat iodomethane was added dropwise. Reaction mixture was stirred for additional 12 hours at −50 to −20° C. and then quenched by adding saturated solution of ammonium chloride while still cold. The reaction mixture was allowed to warm to ambient temperature and was extracted 3 times with ethyl acetate. The combined organic extracts were dried with MgSO4, filtered, concentrated under reduced pressure, and subjected to flash chromatography on silica gel.

To a round bottom flask was added an oxazalidinone derived imide (0.418 mmol, 1.0 eq), THF (0.25 M) and distilled water (1M). This solution was cooled to 0° C. before the slow addition of $H_2O_2$ (35 wt. % in water, 4 eq) followed by the addition of LiOH (2.7 M in water, 1.6 eq). The reaction solution was allowed to warm to room temperature. Progress was followed by LC/MS and the reaction solution was quenched at 0° C. by the addition of saturated Na2SO3 once starting material had been consumed.

The pH was adjusted to about 5-6 with 1N HCl and then the mixture was extracted with EtOAc and methylene chloride. The combined organics were dried over sodium sulfate, filtered, and concentrated. The crude product was purified using silica gel chromatography.

Propylphosphonic anhydride (1.5 eq, 50 wt. % solution in ethyl acetate) was added to solution of carboxylic acid (1 eq) and pyridine (3 eq) in ethyl acetate (0.1 M) at ambient temperature. Reaction mixture was stirred for 5 min and then 4-chloroaniline (1.5 eq) was added. The reaction was stirred at ambient temperature until complete consumption of the acid, which was determined by TLC and/or LC-MS. Reaction mixture was poured in water, 1M NaOH (10 eq) was added, and aqueous layer was extracted with ethyl acetate three times. The combined organic extracts were dried with MgSO4 and concentrated in vacuo. The crude residue was purified using silica gel chromatography (0% to 100% ethyl acetate in hexanes) to afford the amorphous (R)—N-(4-chlorophenyl)-2-(cis-4-(6-fluoroquinolin-4-yl)cyclohexyl) propanamide BMS 986205. The experimental instruments and test conditions used in this application are as follows:

X-Ray Powder Diffractometer (XRPD)
Model: Bruker, Germany, BRUKER D8 DISCOVER
Method: Cu target Ka, voltage 40 KV, current 40 mA, test angle 3-45°, step size 0.02, exposure time 0.2 S, light pipe slit width 1 mm, detector slit width 2.7 mm.
Single-Crystal X-Ray Diffractometer (SXRD)
Model: Bruker, Germany, BRUKER D8 QUEST
Method: Cu target, voltage 40 KV, current 30 mA
Differential Scanning Calorimeter (DSC)
Model: TA Instruments, USA, TA 250
Method: heating rate 10° C./min
Thermogravimetric Analyzer (TGA)
Model: TA Instruments, USA, TA 550
Method: heating rate 10° C./min
DVS
Model: SMS, U.K, DVS intrinsic
Method: 25° C., 10% humidity per step, the judgment standard is less than 0.002% for 10 min Light Incubator Model: Shanghai Yiheng Scientific Instrument Co., Ltd., MGC-100

Ultrasonic Equipment

Model: KQ-3200 (Shanghai Alloy Ultrasonic Equipment Co., Ltd.) Constant temperature shaking incubator Model: ZWY-103B (Shanghai Zhicheng Analytical Instrument Manufacturing Co., Ltd.)

Electrothermal Constant-Temperature Dry Box

Model: DHG-9011A (Shanghai Jinghong Experimental Equipment Co., Ltd.) Programmable drug stability constant temperature and humidity tester Model: CMA-100C (Shanghai Puhan Precision Equipment Co., Ltd.)

Precision Balance

Model: XSE105 (METTLER TOLEDO)

Embodiment 1

30 mg of amorphous active pharmaceutical ingredient was added to a sample bottle, followed by the addition of 5 ml of water. After heating to 90° C. and stirring for 2.5 h, the mixture was filtered to obtain a solidified solid, and the solidified solid was pulverized and added to 5 ml of 90° C. solution of methanol, water and surfactant, wherein the surfactant was sodium dodecylbenzenesulfonate (Adamas), and the volume ratio of methanol to water was 5:1. The surfactant was added with a pipette (the volume ratio of the surfactant to the solvent was 1000:1), the mixture was stirred for 12 hours and filtered, and the filtered product was washed with water and vacuum-dried to give a white crystal S1, crystalline Form B. The X-ray powder diffraction pattern is shown in FIG. 1, and has the following characteristic peaks,

TABLE 1

Table of diffraction angle positions

| 2-Theta | I % |
|---------|-----|
| 6.985   | 1.7 |
| 9.447   | 10.4 |
| 12.398  | 43.8 |
| 13.677  | 20.1 |
| 17.171  | 32.2 |
| 17.644  | 89.2 |
| 18.985  | 6.5 |
| 20.142  | 100 |
| 21.118  | 42.8 |
| 21.62   | 36.3 |
| 22.199  | 25.1 |
| 24.173  | 8.8 |
| 24.915  | 7.8 |
| 26.828  | 21.9 |
| 28.682  | 6.8 |
| 30.418  | 6.6 |
| 31.46   | 5.8 |

Figure 3:
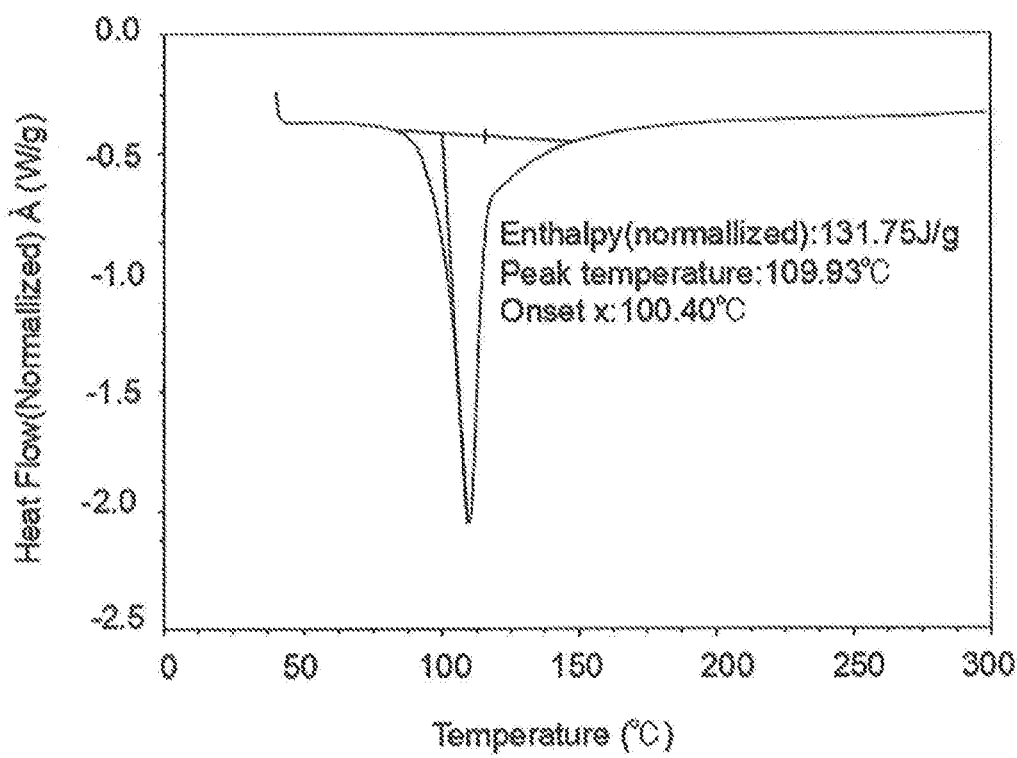
FIG. 3 is a DSC pattern of Form B of Embodiment 1.
Figure 4:
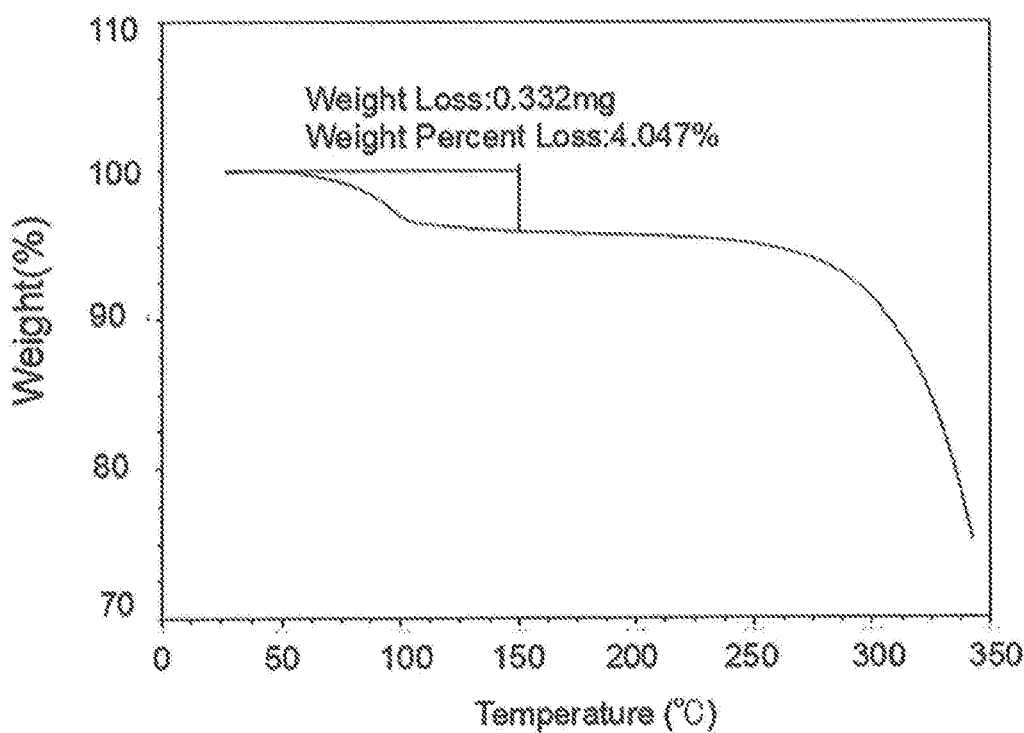
FIG. 4 is a TGA pattern of Form B of Embodiment 1.

Further DSC and TGA results are shown in FIGS. 3 and 4, where there is an endothermic peak at 109.93° C. in the DSC pattern, and the weight loss of the first phase in the TGA pattern is 4.047%, which is close to the theoretical value 4.2% of the water in the monohydrate, indicating that it is a crystalline compound containing one molecule of water.

Embodiment 2

Figure 5:
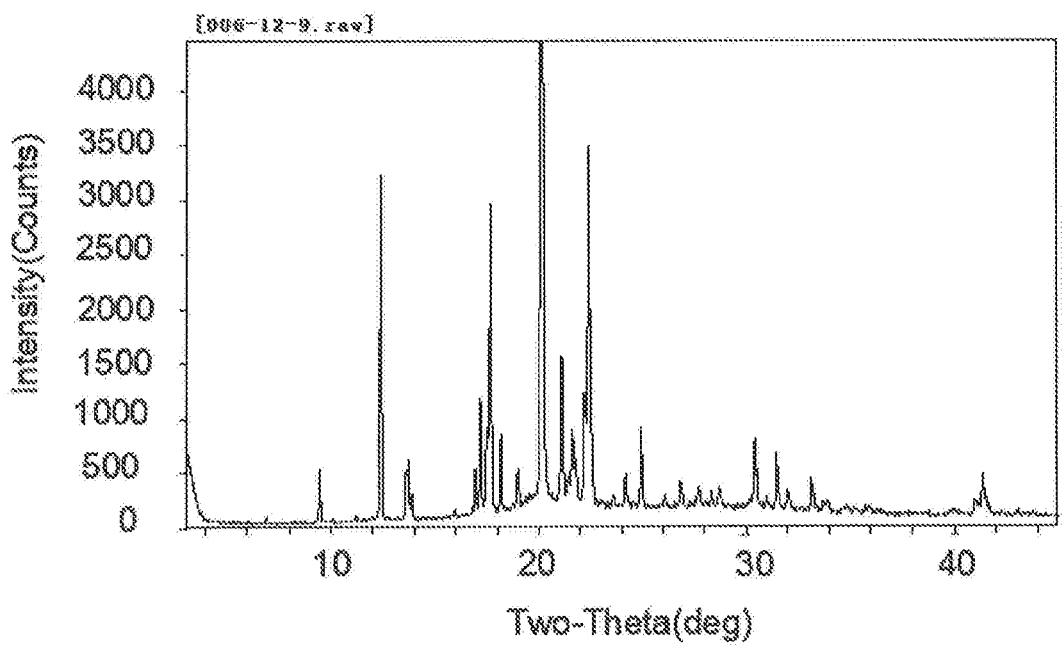
FIG. 5 is an X-ray powder diffraction pattern of Form B of Embodiment 2.

10 mg of amorphous active pharmaceutical ingredient was added to a sample bottle, followed by the addition of tetrahydrofuran and water, wherein the volume ratio of tetrahydrofuran to water was 1:4. The solution was added to 0.5 mg of the final product S1 in Embodiment 1, shaken in a 50° C. shaker for 48 h, and filtered to obtain a solid. The solid was washed with water, and vacuum-dried to give a white crystal S2, crystalline Form B. Its XRPD pattern is shown in FIG. 5, which coincides with the XRPD pattern of S1 in Embodiment 1.

Embodiment 3

Figure 6:
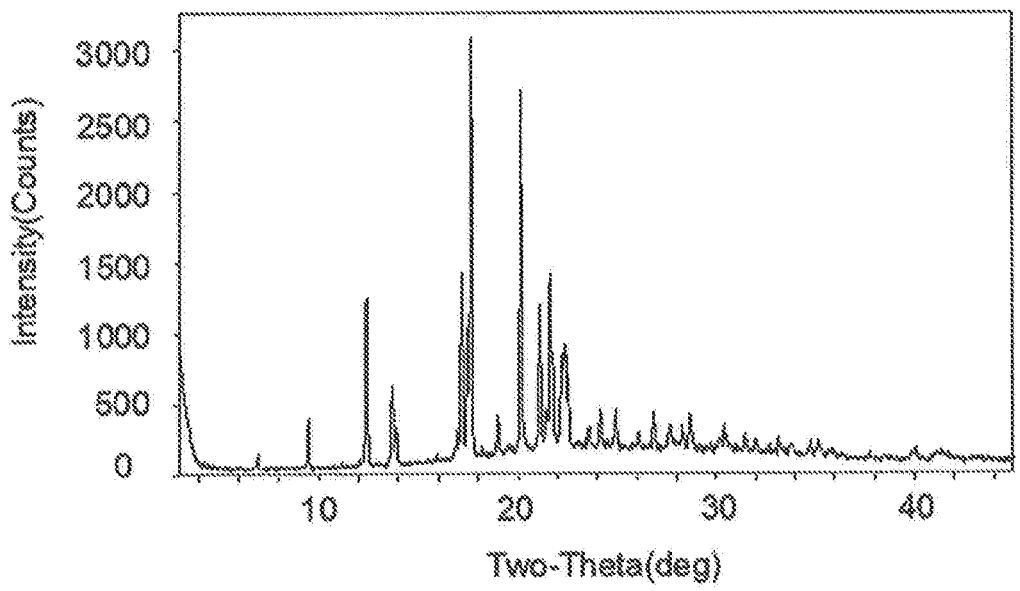
FIG. 6 is an X-ray powder diffraction pattern of Form B of Embodiment 3.

10 mg of amorphous active pharmaceutical ingredient was added to a sample bottle, followed by the addition of acetone and water, wherein the volume ratio of acetone to water was 1:4. The solution was added to 0.5 mg of the final product S1 in Embodiment 1, shaken in a 50° C. shaker for 48 h, and filtered to obtain a solid. The solid was washed with water, and vacuum-dried to give a white crystal S3, crystalline Form B. Its XRPD pattern is shown in FIG. 6, which coincides with the XRPD pattern of S1 in Embodiment 1.

Embodiment 4

Figure 7:
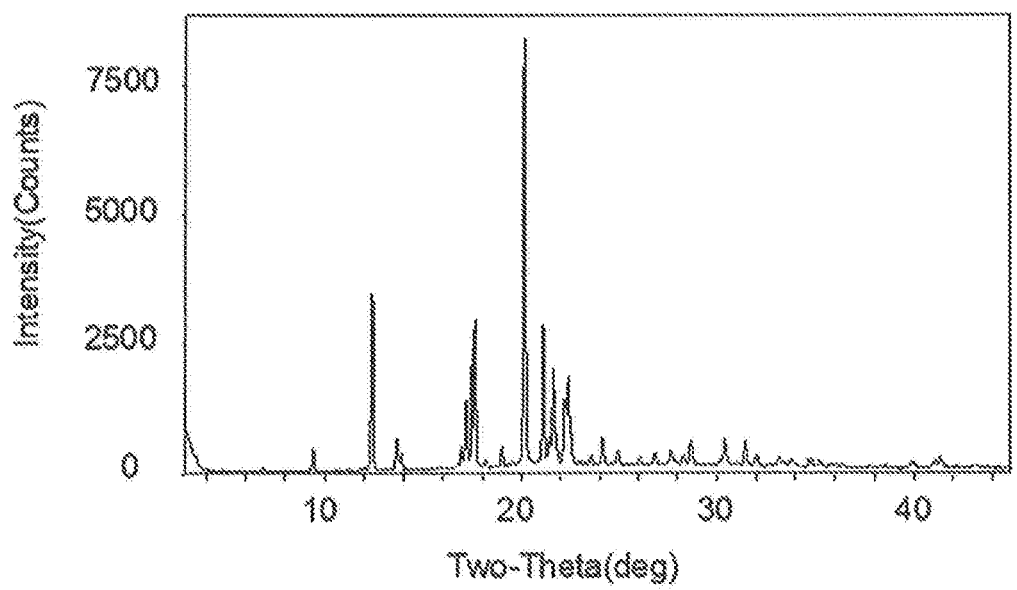
FIG. 7 is an X-ray powder diffraction pattern of Form B of Embodiment 4.

10 mg of amorphous active pharmaceutical ingredient was added to a sample bottle, followed by the addition of acetonitrile and water, wherein the volume ratio of acetonitrile to water was 1:4. The solution was added to 0.5 mg of the final product S1 in Embodiment 1, shaken in a 50° C. shaker for 48 h, and filtered to obtain a solid. The solid was washed with water, and vacuum-dried to give a white crystal S4, crystalline Form B. Its XRPD pattern is shown in FIG. 7, which coincides with the XRPD pattern of S1 in Embodiment 1.

Embodiment 5

Figure 2:
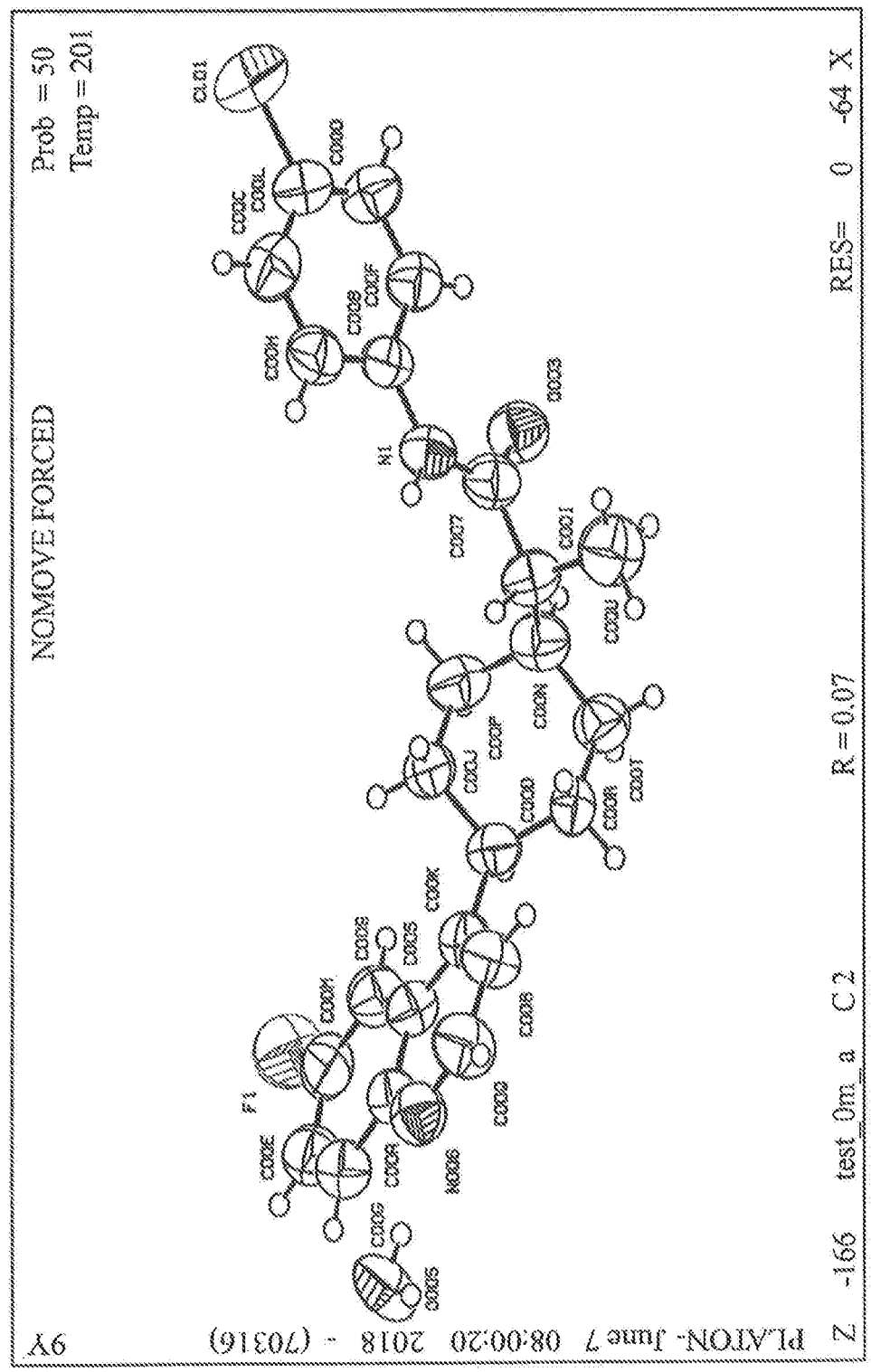
FIG. 2 is a single crystal molecular structure ellipsoid diagram of Form B of Embodiment 1.
Figure 8:
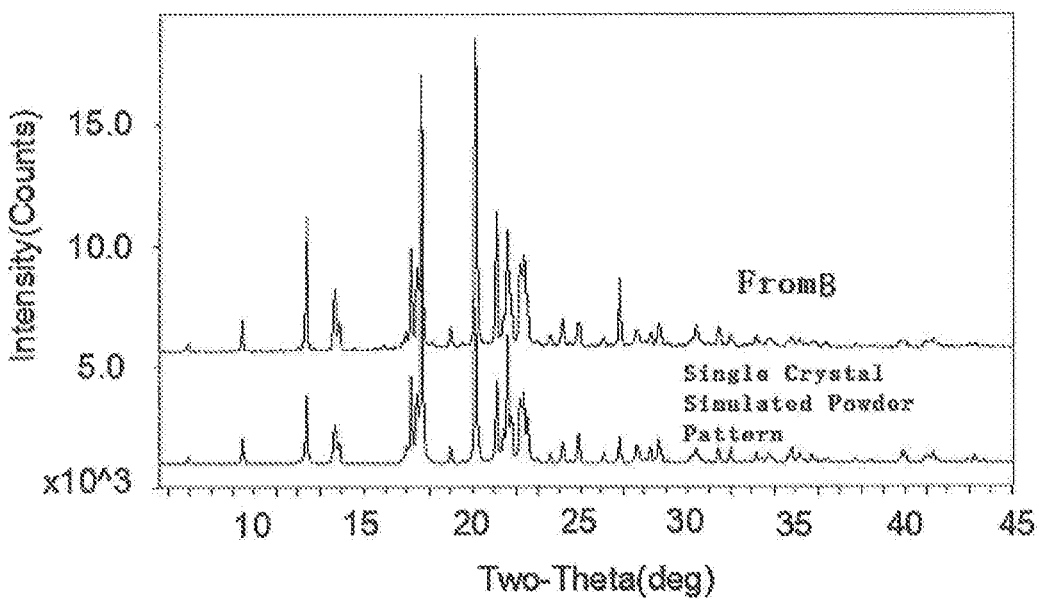
FIG. 8 is an XRPD comparison diagram of the single crystal of Embodiment 5 and Form B of Embodiment 1.

20 mg of final product S1 in Embodiment 1 was weighed, 5 ml of 10° C. methanol aqueous solution (volume ratio 1:4) was added, and the mixture was subjected to ultrasonic treatment for 1 s (frequency 40 KHz, power 200 W) to ensure a very small amount of solid observed in the solution by naked eyes. The mixture was placed in a 5° C. environment, a hole (d 0.2 mm) was punched out by a hole puncher after the sample bottle was sealed, and slow volatilization was performed for 25 days to give a single crystal of Form B. The single crystal was detected by a single-crystal X-ray diffractometer for crystallographic structural analysis. The single crystal data is shown in Table 2 below, and the single crystal molecular structure ellipsoid diagram is shown in FIG. 2. The XRPD comparison diagram of the single crystal of this embodiment and Form B of Embodiment 1 is as shown in FIG. 8. Their XRPD is highly consistent, indicating that Form B of the present invention is a single crystal.

TABLE 2

Single Crystal Data

| Empirical formula | $C_{24}H_{26}ClFN_2O_2$ | |
|---|---|---|
| Formula weight | 428.92 | |
| Temperature | 201(2) K | |
| Wavelength | 1.54178 Å | |
| Crystal system | Monoclinic | |
| Space group | C2 | |
| Unit cell dimensions | a = 25.358(9) Å | α = 90°. |
| | b = 10.016(3) Å | β = 91.57(2)°. |
| | c = 8.788(3) Å | γ = 90°. |

TABLE 2-continued

Single Crystal Data

| | |
|---|---|
| Volume | 2231.2(14) Å³ |
| Z | 4 |

Embodiment 6

Figure 21:
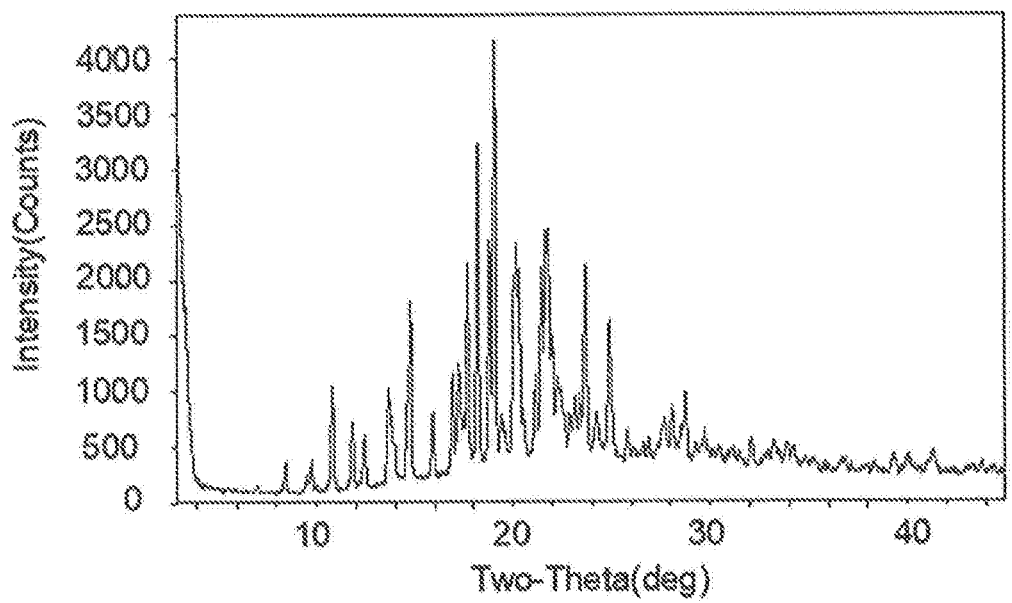
FIG. 21 is an X-ray powder diffraction pattern of Form C of Embodiment 6.

30 mg of amorphous active pharmaceutical ingredient was added to a sample bottle, followed by the addition of 5 mg of water. The mixture was heated to 90° C., stirred for 2.5 h and filtered to obtain a solidified solid. The solidified solid was pulverized, and added to 5 ml of 90° C. methanol aqueous solution, wherein the volume ratio of methanol to water was 5:1. The mixture was stirred for 12 h, and filtered. The filtered product was washed with water and vacuum-dried to give a crystal S6, Form C. The X-ray powder diffraction pattern is shown in FIG. 21, and has the following characteristic peaks,

| 2-Theta | I % |
|---|---|
| 8.465 | 4.5 |
| 9.733 | 5 |
| 10.804 | 24.6 |
| 11.818 | 15.9 |
| 12.419 | 12.7 |
| 13.656 | 22.5 |
| 14.772 | 42.6 |
| 15.926 | 14.9 |
| 16.93 | 23 |
| 17.247 | 24.3 |
| 17.688 | 48.1 |
| 18.203 | 75.2 |
| 18.823 | 52.5 |
| 19.066 | 100 |
| 20.144 | 45.8 |
| 21.16 | 13.2 |
| 21.779 | 52.9 |
| 22.26 | 13.3 |
| 23.694 | 43.1 |
| 24.234 | 8.5 |
| 24.93 | 32.4 |
| 27.703 | 8 |
| 28.047 | 12.6 |
| 28.743 | 14.7 |
| 32.062 | 6.3 |

Figure 22:
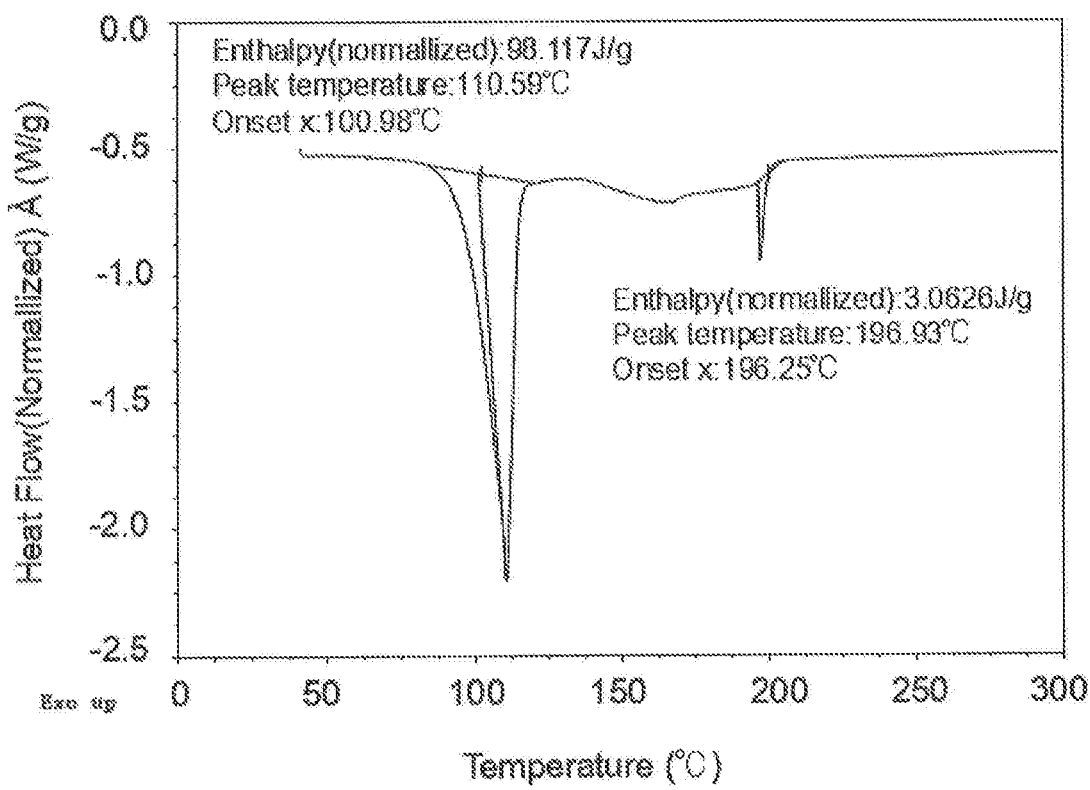
FIG. 22 is a DSC pattern of Form C of Embodiment 6.
Figure 23:
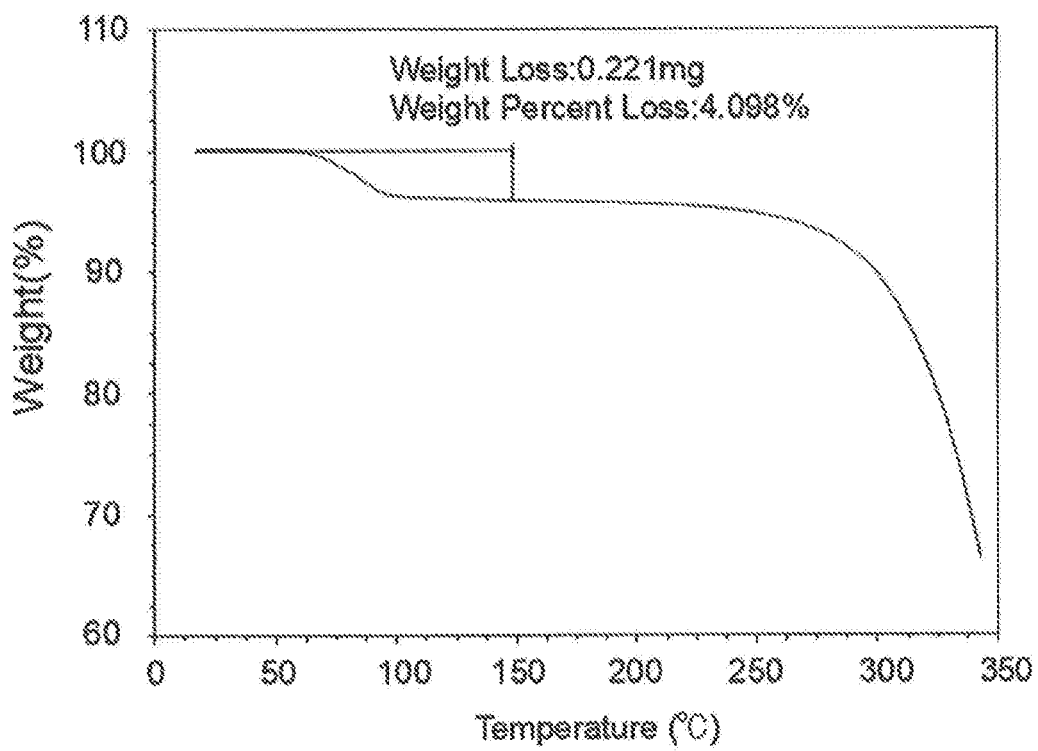
FIG. 23 is a TGA pattern of Form C of Embodiment 6.

Further DSC and TGA results are shown in FIGS. 22 and 23, where there are endothermic peaks at 110.59° C. and 196.93° C. in the DSC pattern, and the weight loss of the first phase in the TGA pattern is 4.098%, which is close to the theoretical value 4.2% of the water in the monohydrate, indicating that it is a crystalline compound containing one molecule of water.

Embodiment 7

Figure 24:
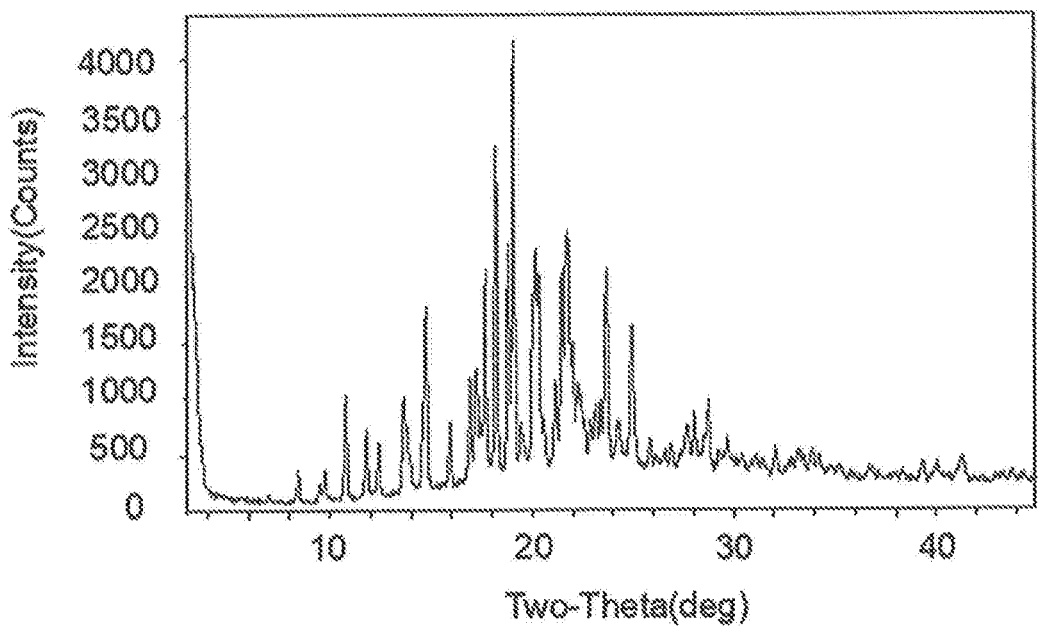
FIG. 24 is an X-ray powder diffraction pattern of Form C of Embodiment 7.

30 mg of amorphous active pharmaceutical ingredient was added to a sample bottle, followed by the addition of 5 mg of water. The mixture was heated to 90° C., stirred for 2.5 h and filtered to obtain a solidified solid. The solidified solid was pulverized, and added to 5 ml of 90° C. methanol aqueous solution, wherein the volume ratio of methanol to water was 8:1. The mixture was stirred for 12 h, and filtered. The filtered product was washed with water and vacuum-dried to give a crystal, Form C. Its XRPD pattern coincides with the XRPD pattern of S6 in Embodiment 6. The X-ray powder diffraction pattern is shown in FIG. 24.

Embodiment 8

Figure 25:
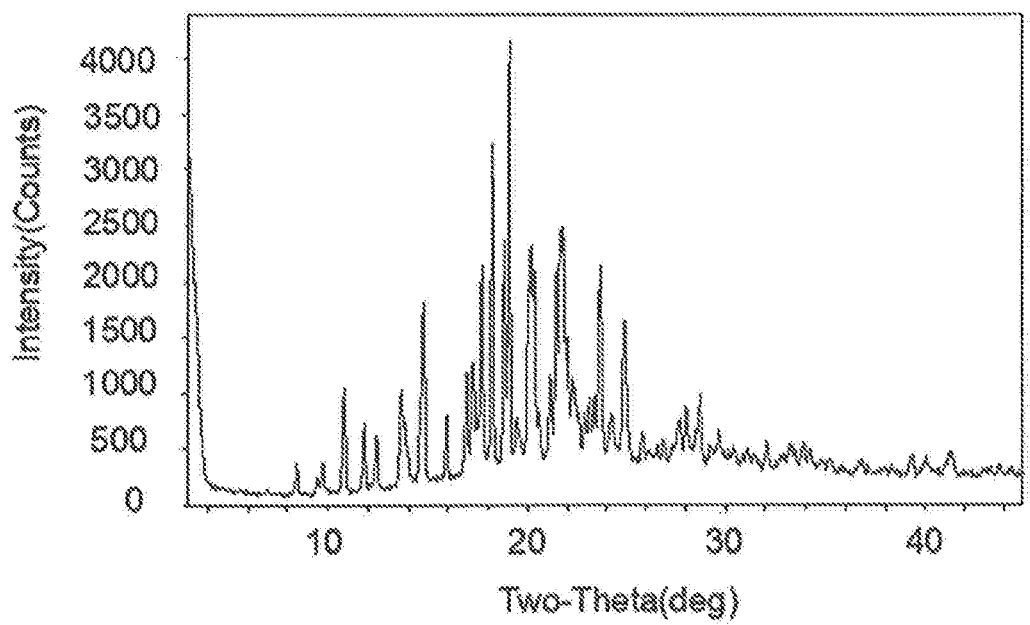
FIG. 25 is an X-ray powder diffraction pattern of Form C of Embodiment 8.

30 mg of amorphous active pharmaceutical ingredient was added to a sample bottle, followed by the addition of 5 mg of water. The mixture was heated to 90° C., stirred for 2.5 h and filtered to obtain a solidified solid. The solidified solid was pulverized, and added to 5 ml of 90° C. methanol aqueous solution, wherein the volume ratio of methanol to water was 6:1. The mixture was stirred for 12 h, and filtered. The filtered product was washed with water and vacuum-dried to give a crystal, Form C. Its XRPD pattern coincides with the XRPD pattern of S6 in Embodiment 6. The X-ray powder diffraction pattern is shown in FIG. 25.

Embodiment 9

Figure 26:
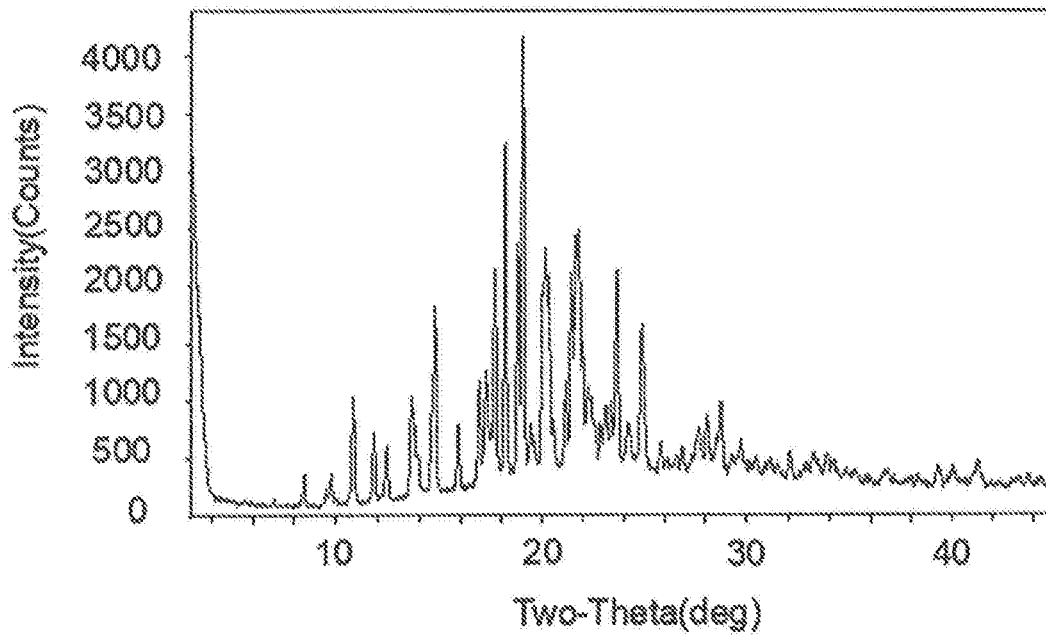
FIG. 26 is an X-ray powder diffraction pattern of Form C of Embodiment 9.

30 mg of amorphous active pharmaceutical ingredient was added to a sample bottle, followed by the addition of 5 mg of water. The mixture was heated to 90° C., stirred for 2.5 h and filtered to obtain a solidified solid. The solidified solid was pulverized, and added to 5 ml of 90° C. methanol aqueous solution, wherein the volume ratio of methanol to water was 7:1. The mixture was stirred for 12 h, and filtered. The filtered product was washed with water and vacuum-dried to give a crystal, Form C. Its XRPD pattern coincides with the XRPD pattern of S6 in Embodiment 6. The X-ray powder diffraction pattern is shown in FIG. 26.

Comparative Embodiment 1

Figure 9:
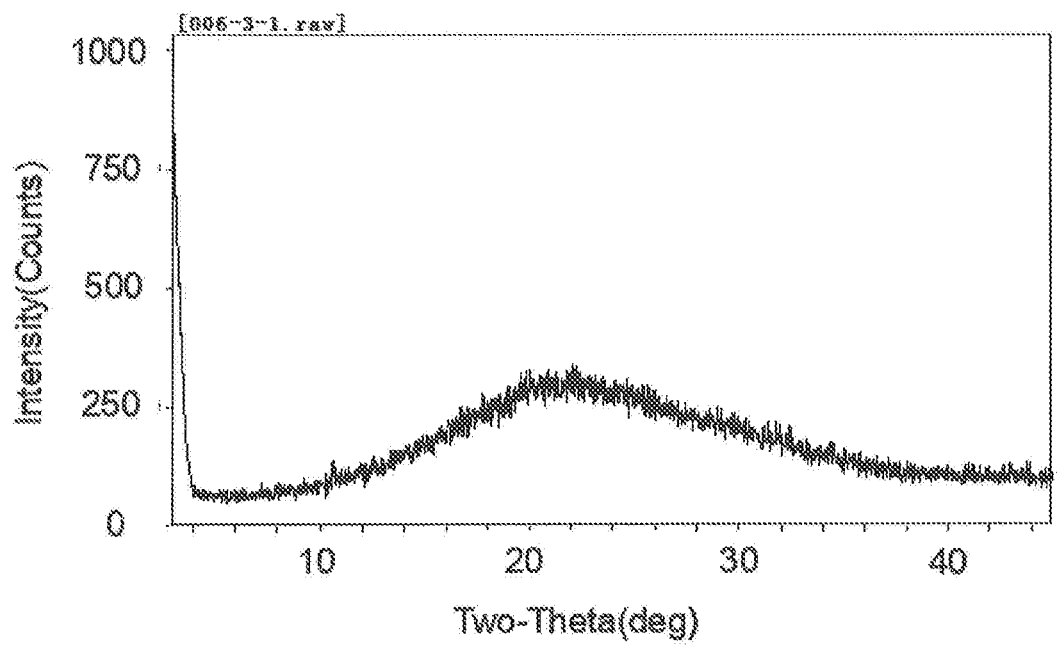
FIG. 9 is an X-ray powder diffraction pattern of the amorphous product of Comparative Embodiment 1.

15 mg of amorphous active pharmaceutical ingredient was weighed, followed by the addition of 1.5 ml of methanol, 1.5 ml of ethanol, 1 ml of ethyl acetate and 0.8 ml of dichloromethane. After dissolving, the solution was evaporated to remove the solvent, and dried to give the amorphous product D1. The XRPD pattern is shown in FIG. 9.

Comparative Embodiment 2

Figure 10:
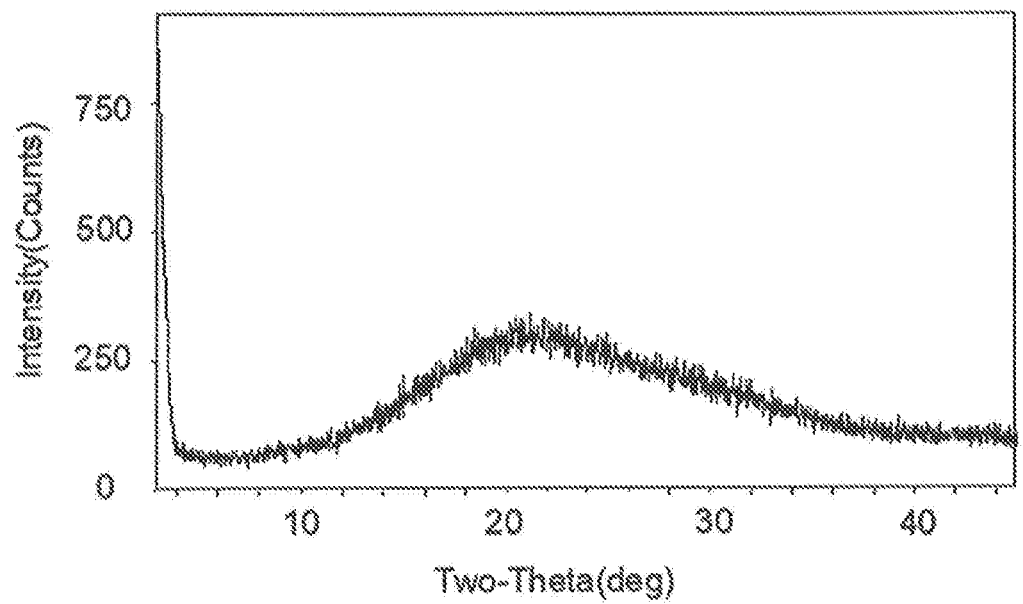
FIG. 10 is an X-ray powder diffraction pattern of the amorphous product of Comparative Embodiment 2.

500 mg of amorphous active pharmaceutical ingredient was weighed, followed by the addition of 7 ml of ethyl acetate. The mixture was heated to 70° C. for dissolution, stirred for 30 min, and cooled to room temperature to precipitate a white solid D2. The XRPD pattern is shown in FIG. 10.

Experimental Test Method

The products prepared in Embodiment 1 and Embodiment 6, and the amorphous active pharmaceutical ingredient were respectively subjected to experimental tests for light stability, high-temperature stability, accelerated stability, high-humidity stability, and water adsorption.

Figure 11:
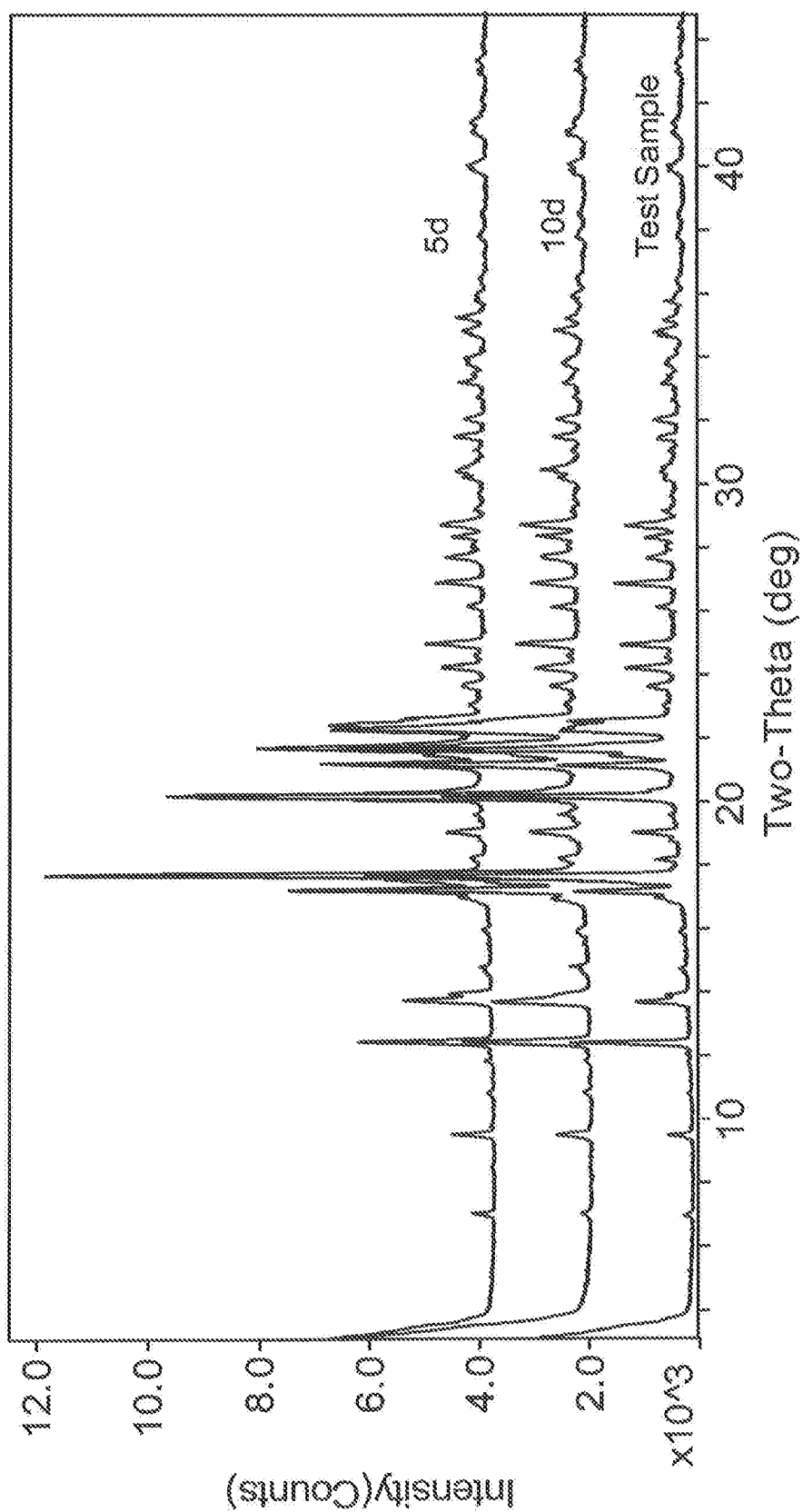
FIG. 11 is an XRPD comparison diagram of light stability of Form B of Embodiment 1.
Figure 12:
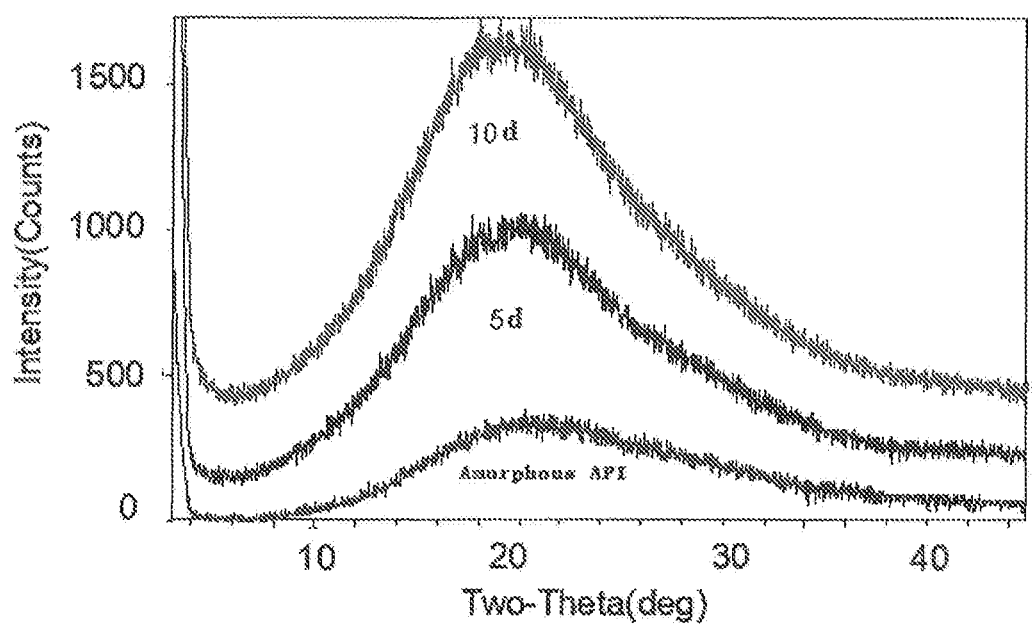
FIG. 12 is an XRPD comparison diagram of light stability of the amorphous active pharmaceutical ingredient.
Figure 27:
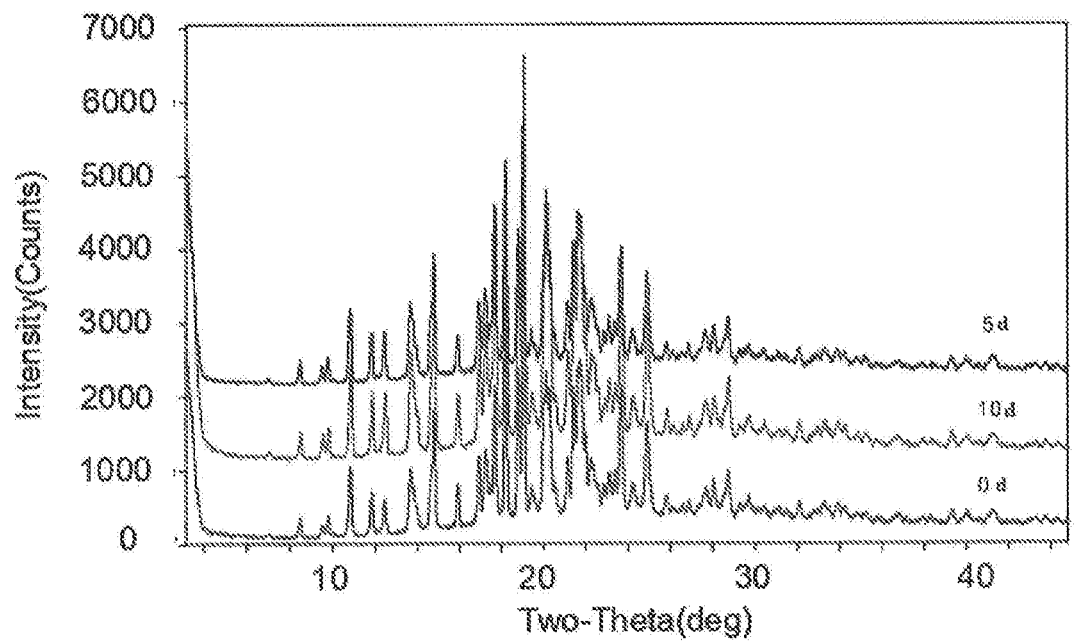
FIG. 27 is an XRPD comparison diagram of light stability of Form C of Embodiment 6.

(1) The test products were respectively placed under 25° C. and 4500 lux of light and tested for 5 d and 10 d stability, and the results are shown in FIGS. 11, 12 and 27. The results show that Forms B and C and amorphous have good stability.

Figure 13:
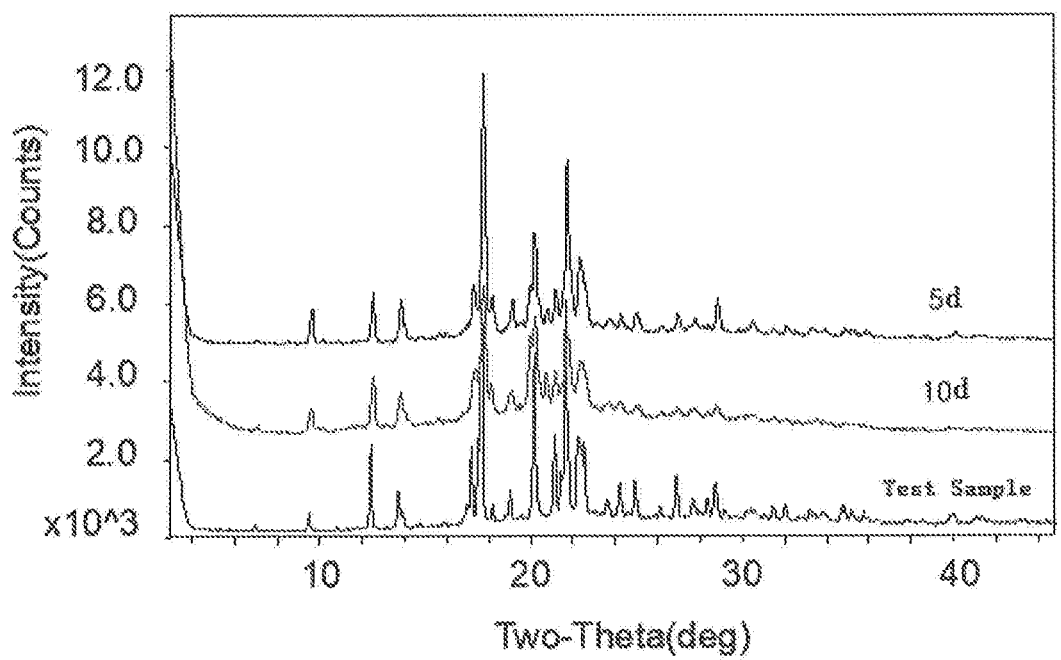
FIG. 13 is an XRPD comparison diagram of high-temperature stability of Form B of Embodiment 1.
Figure 14:
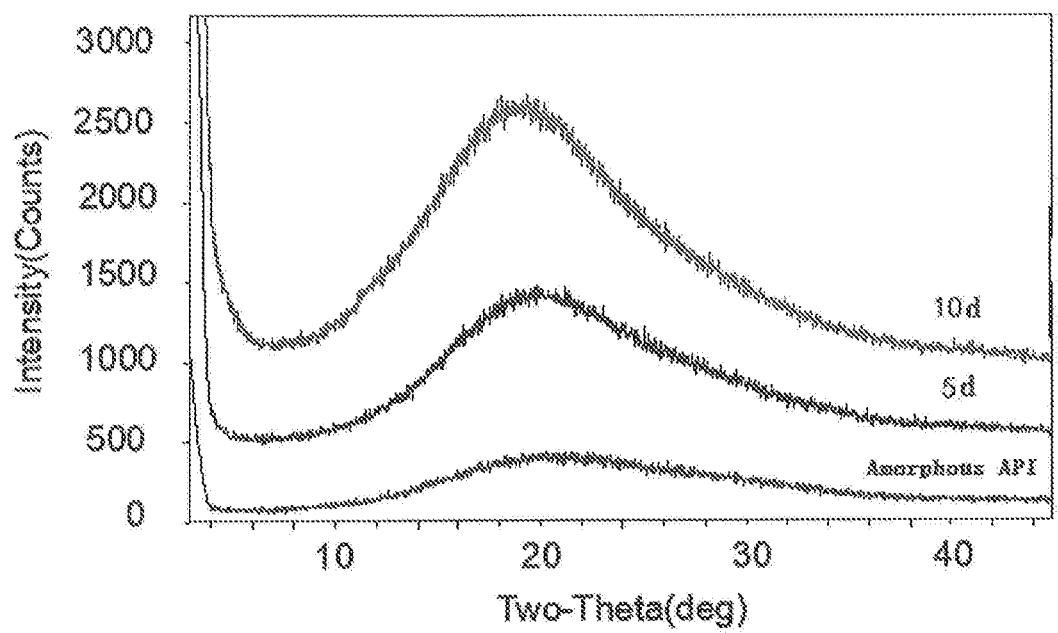
FIG. 14 is an XRPD comparison diagram of high-temperature stability of the amorphous active pharmaceutical ingredient.
Figure 28:
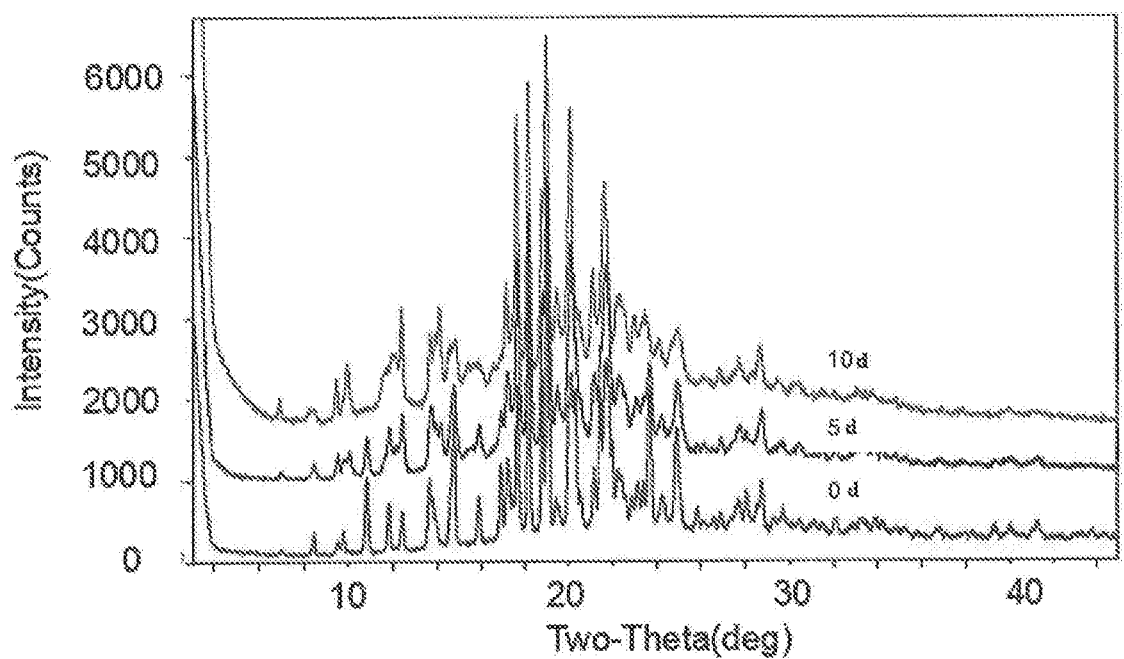
FIG. 28 is an XRPD comparison diagram of high-temperature stability of Form C of Embodiment 6.

(2) The test products were respectively placed under 60° C. and tested for 5 d and 10 d stability, and the results are shown in FIGS. 13, 14 and 28. The results show that Forms B and C and amorphous have good stability.

Figure 15:
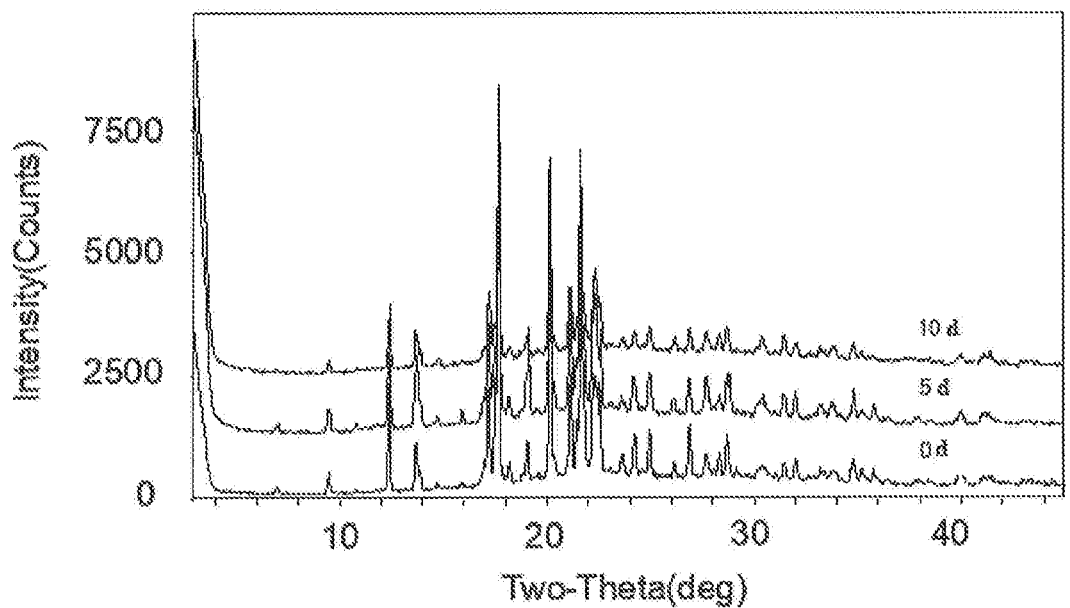
FIG. 15 is an XRPD comparison diagram of accelerated stability of Form B of Embodiment 1.
Figure 16:
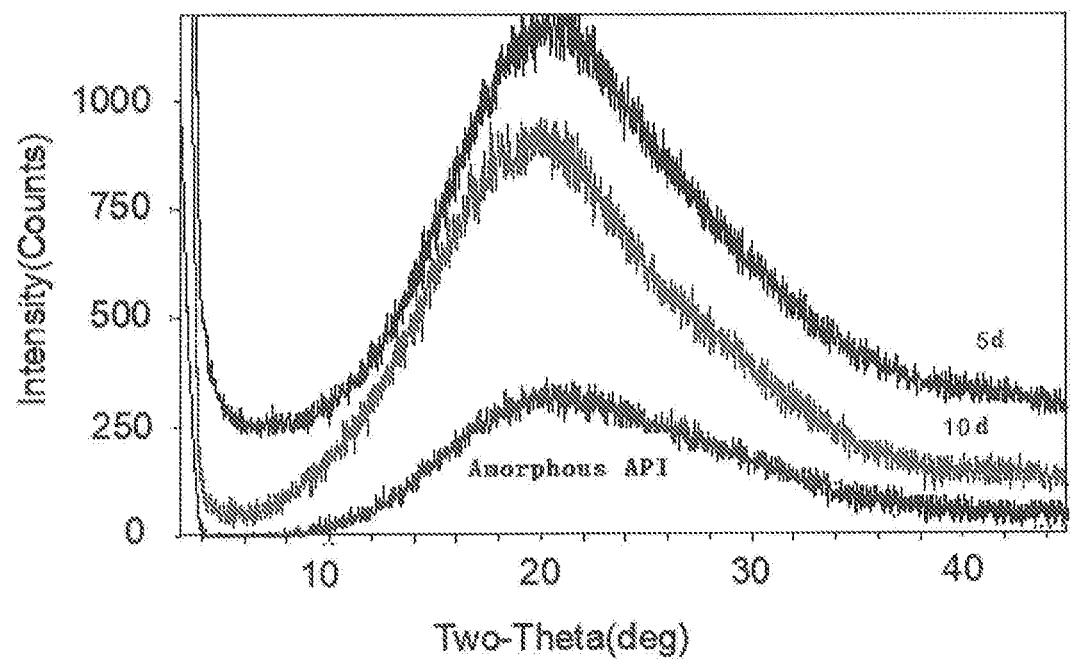
FIG. 16 is an XRPD comparison diagram of accelerated stability of the amorphous active pharmaceutical ingredient.
Figure 29:
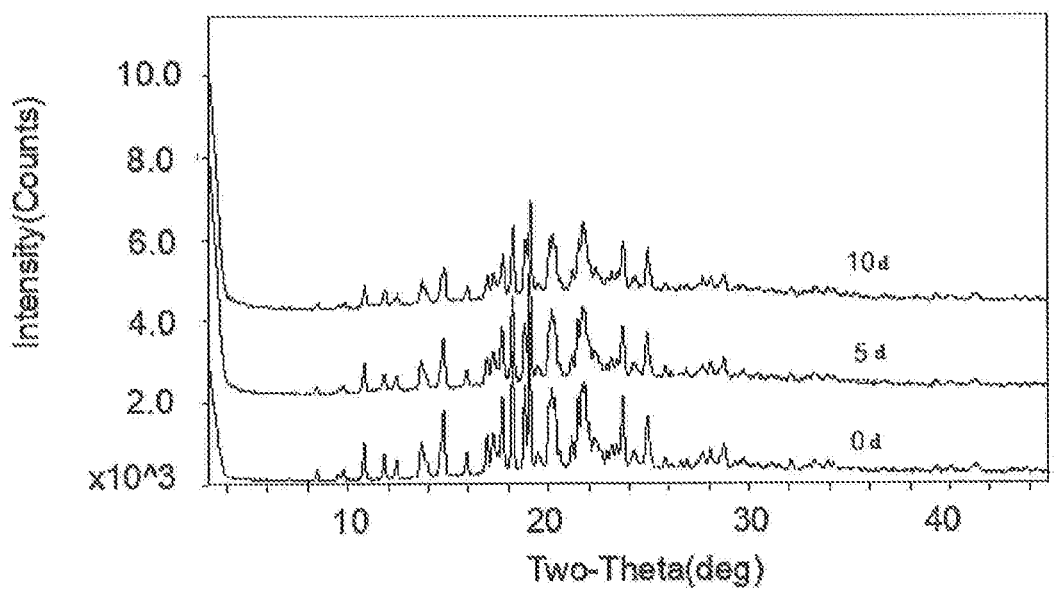
FIG. 29 is an XRPD comparison diagram of accelerated stability of Form C of Embodiment 6.

(3) The test products were respectively placed under 40° C. and humidity of 75% RH, and the results are shown in FIGS. 15, 16 and 29. The results show that Forms B and C and amorphous have good stability.

Figure 32:
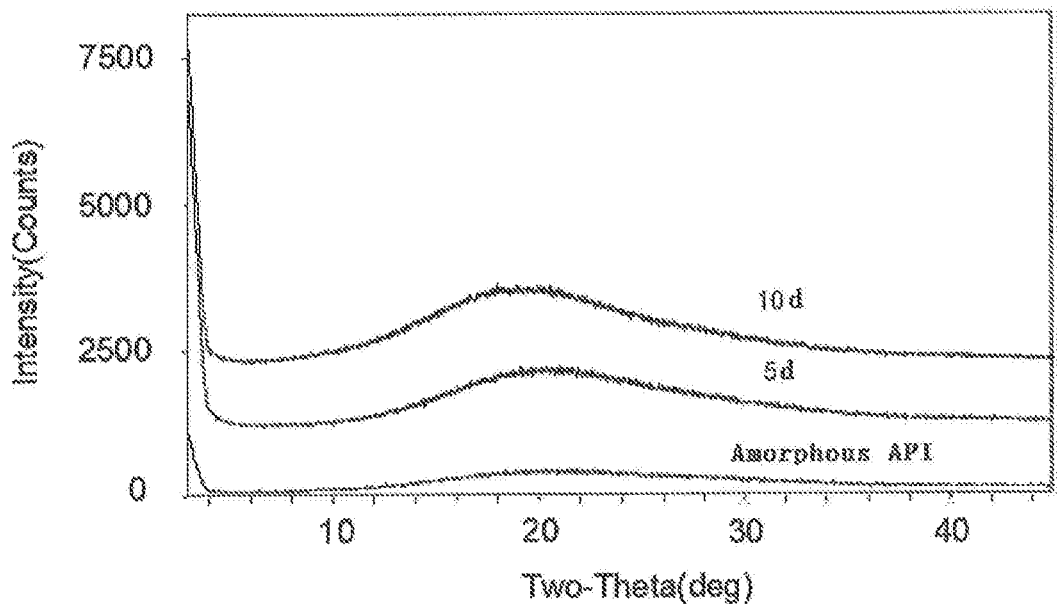
FIG. 32 is an XRPD comparison diagram of high-humidity stability of the amorphous active pharmaceutical ingredient.
Figure 33:
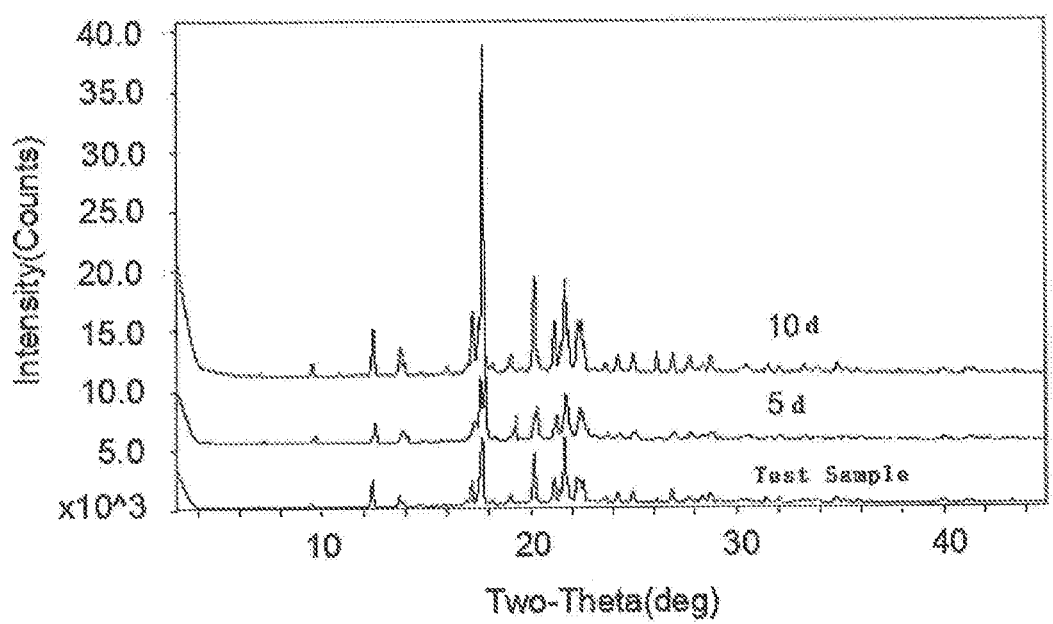
FIG. 33 is an XRPD comparison diagram of high-humidity stability of Form B of Embodiment 1.
Figure 34:
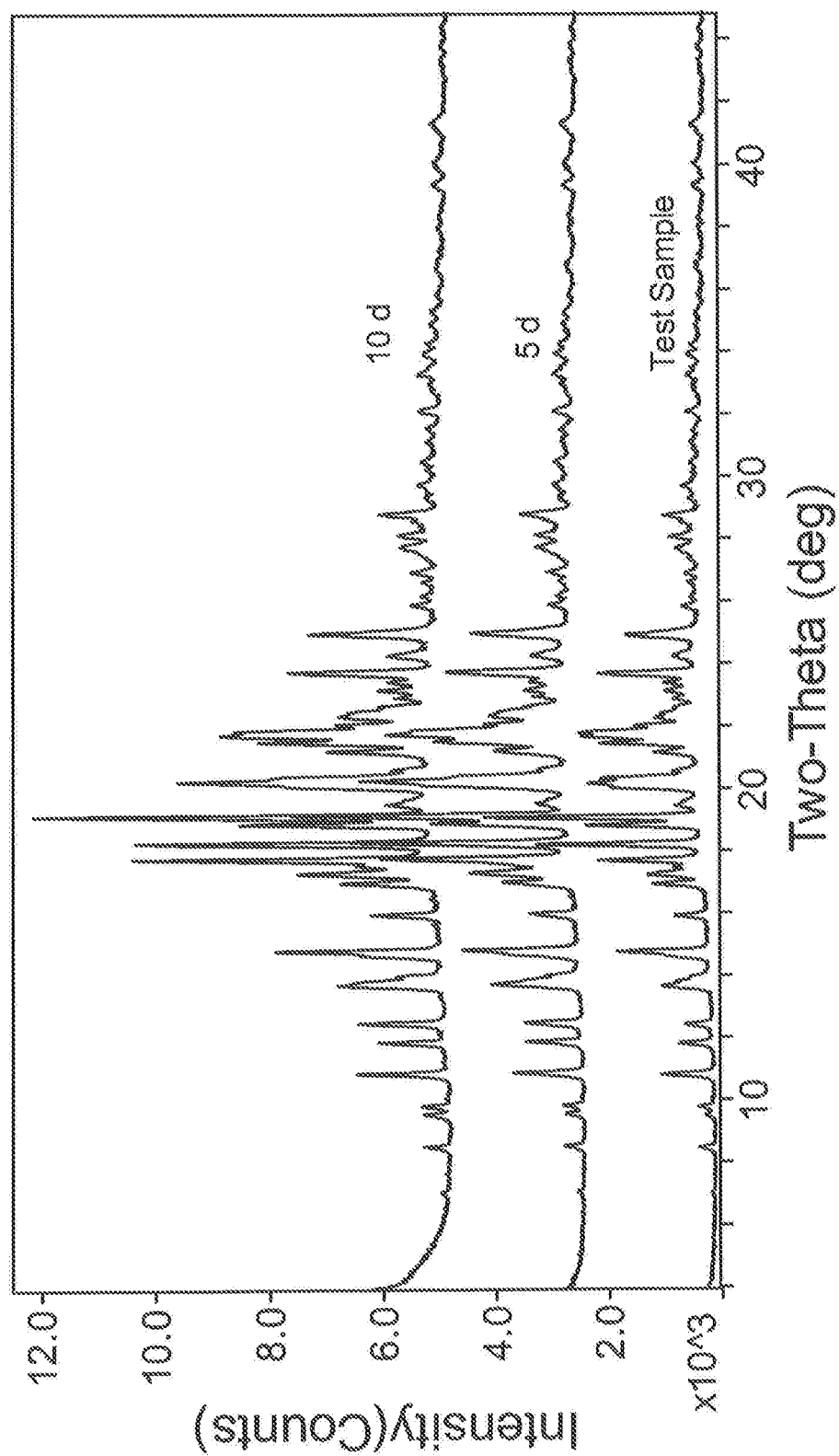
FIG. 34 is an XRPD comparison diagram of high-humidity stability of Form C of Embodiment 6.

(4) The test products were respectively placed under 25° C. and humidity of 92.5% RH, and the results are shown in FIGS. 32, 33 and 34. The results show that Forms B and C and amorphous have good stability.

Figure 17:
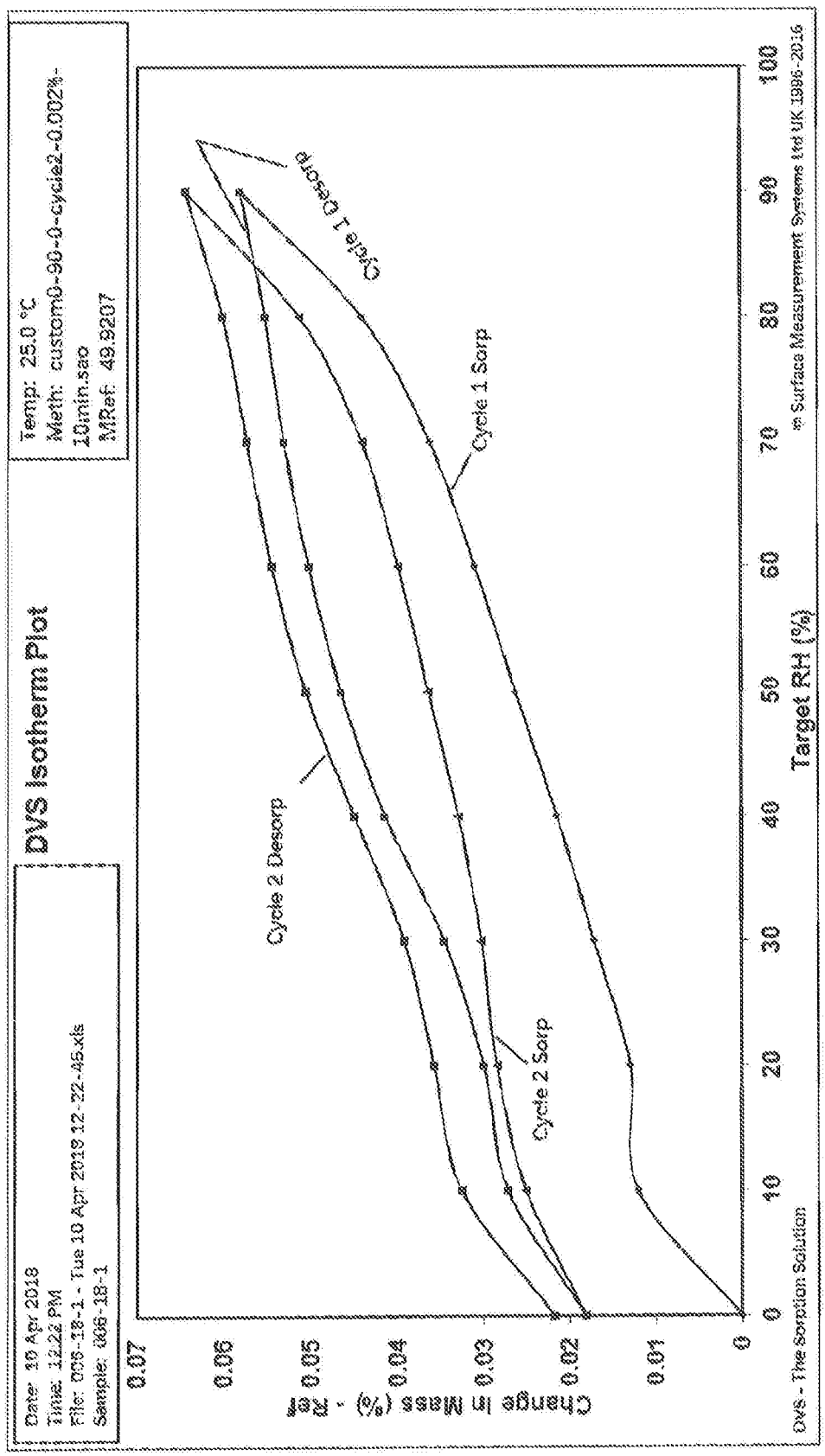
FIG. 17 is a DVS pattern of Form B of Embodiment 1.
Figure 18:
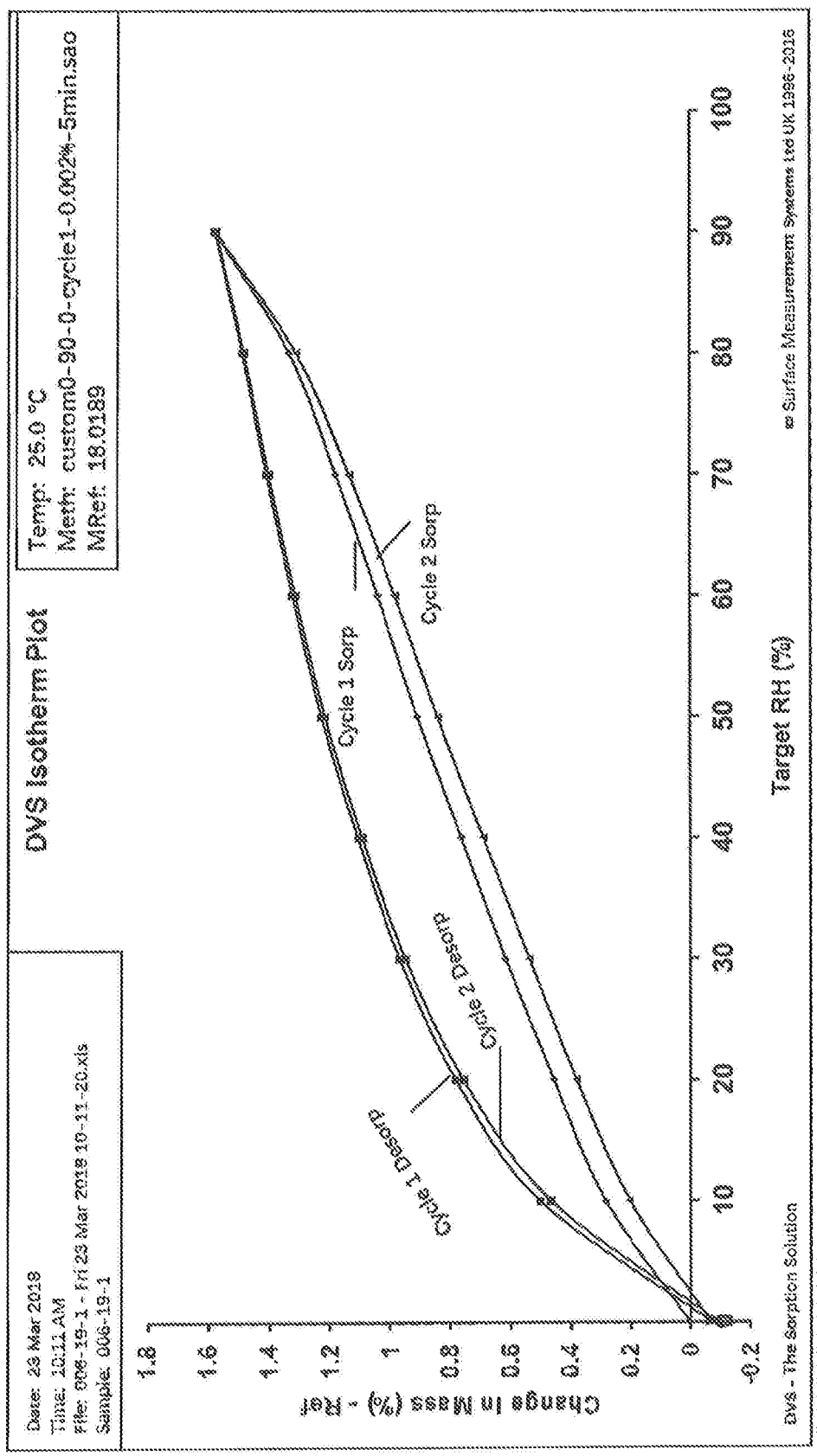
FIG. 18 is a DVS pattern of the amorphous active pharmaceutical ingredient.
Figure 19:
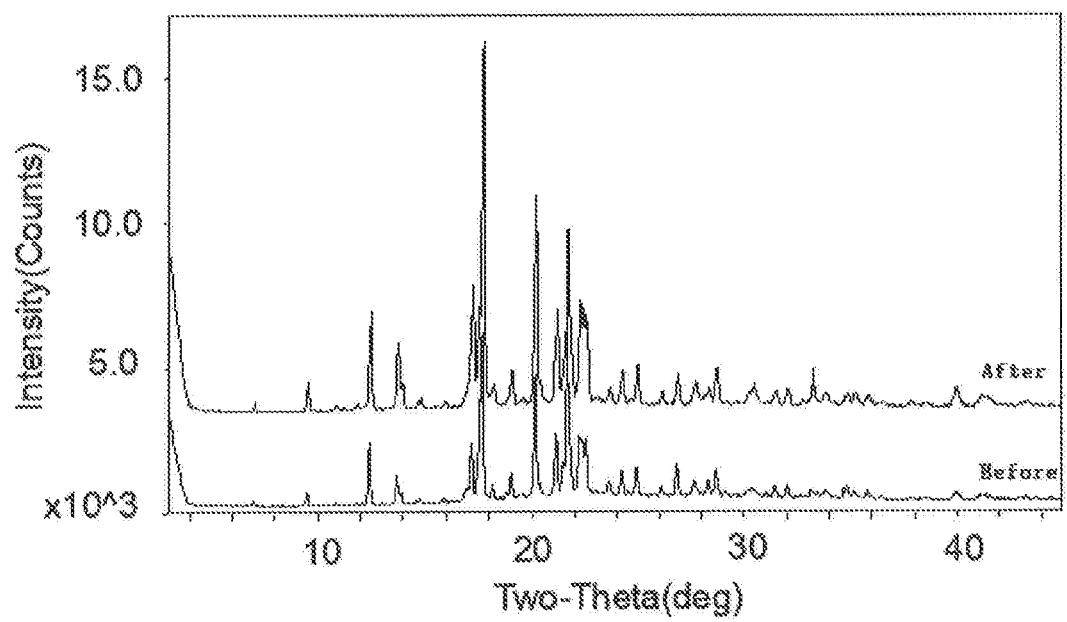
FIG. 19 is an XRPD comparison diagram of Form B of Embodiment 1 before and after DVS detection.
Figure 20:
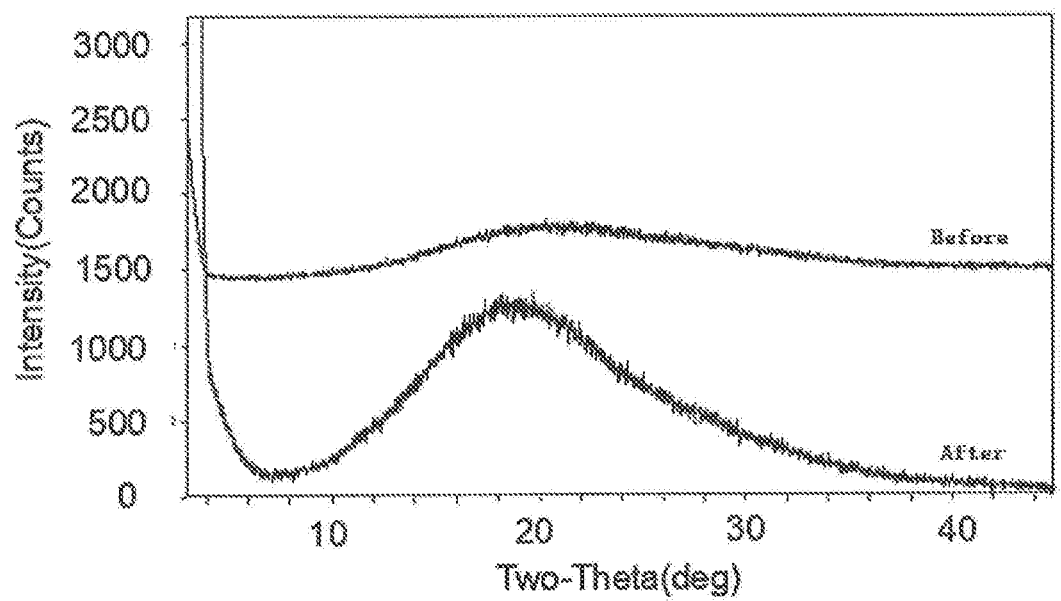
FIG. 20 is an XRPD comparison diagram of the amorphous active pharmaceutical ingredient before and after DVS detection.
Figure 30:
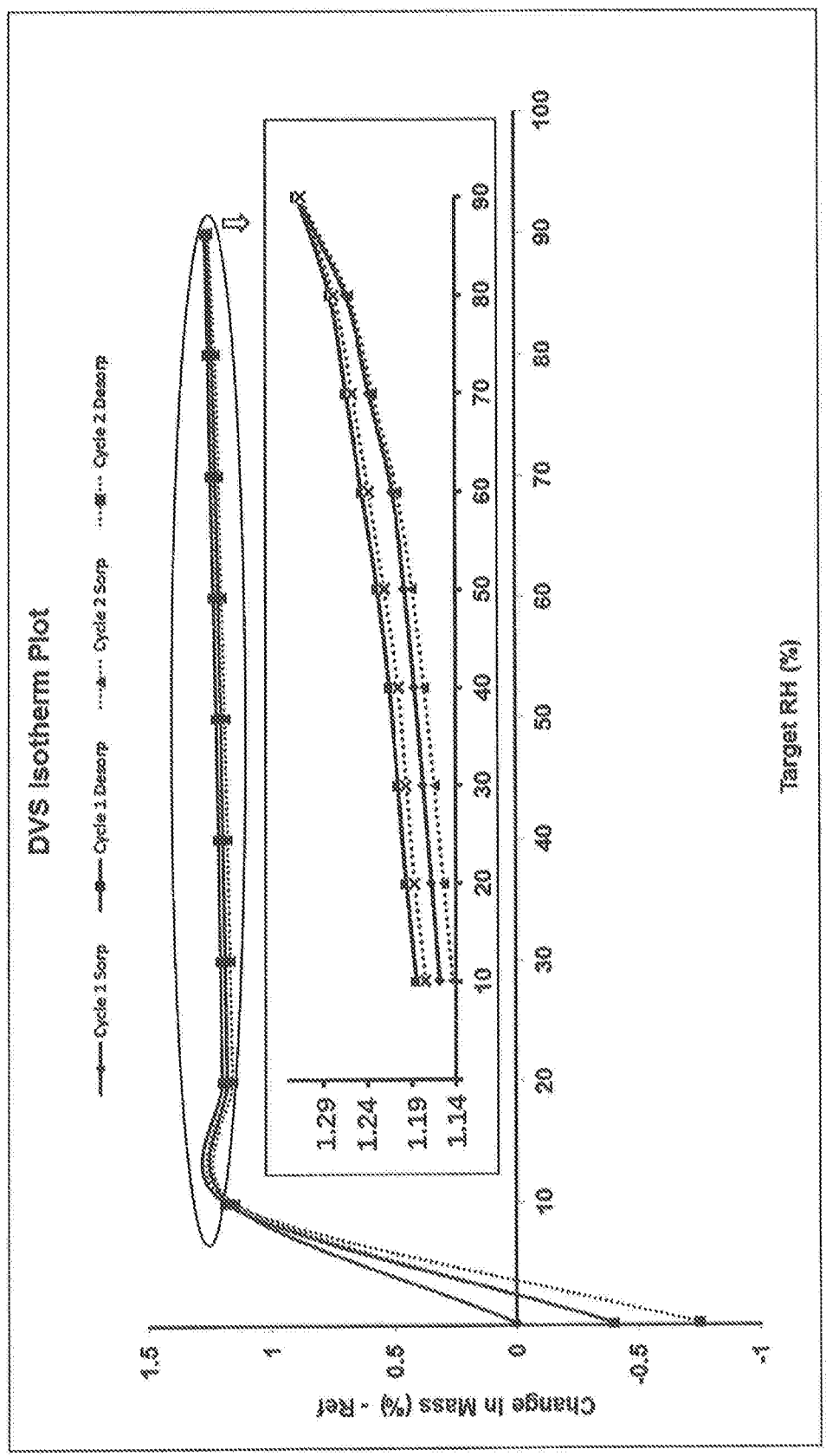
FIG. 30 is a DVS pattern of Form C of Embodiment 6.
Figure 31:
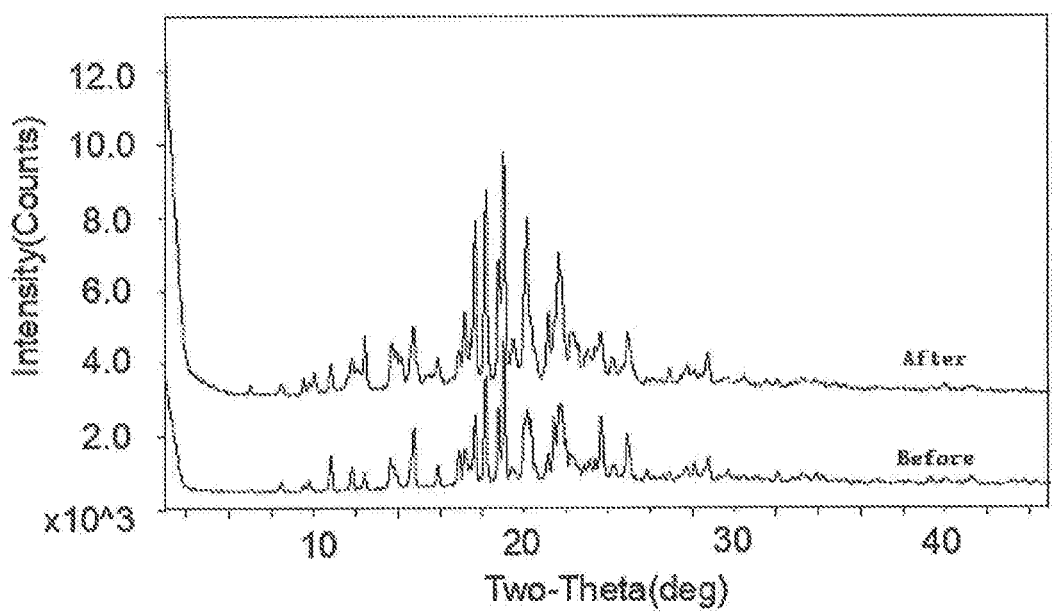
FIG. 31 is an XRPD comparison diagram of Form C of Embodiment 6 before and after DVS detection.

(5) The test products were respectively subjected to the water adsorption test, the experimental conditions were as follows: 25° C., humidity 0-90, 10% per step, and the weight change was less than 0.002% in each step of 10 minutes. The DVS is shown in FIGS. 17, 18 and 30, and the XRPD patterns before and after the detection are shown in FIGS. 19, 20 and 31. The hygroscopic curve indicates that Forms B and C do not adsorb water under the test conditions, and the amorphous active pharmaceutical ingredient has a large hygroscopicity compared with Forms B and C.

It is apparent that the above-described embodiments are merely illustrative of the examples, and are not intended to limit the implementations. Other variations or modifications of the various forms may be made by those skilled in the art in light of the above description. There is no need and no way to exhaust all of the implementations. Obvious changes or variations resulting therefrom are still within the scope of the invention.

The invention claimed is:

1. Form B of crystalline monohydrate (R)—N-(4-chlorophenyl)-2-(cis-4-(6-fluoroquinolin-4-yl)cyclohexyl)propanamide, wherein the Form B is a monoclinic crystal system, the space group is C2, the unit cell dimensions are a=25.358(9) Å, b=10.016(3) Å, c=8.788(3) Å, α=90°, β=91.57(2°), γ=90° and Z=4, and the unit cell volume is 2231.2(14) Å$^3$, and a X-ray powder diffraction pattern mainly has the following characteristic peaks, wherein the X-ray powder diffraction pattern has the strongest peak when 2θ is 20.142±0.2, and has the second strongest peak when 2θ is 17.644±0.2,

| Angle 2θ |
| --- |
| 6.985 ± 0.2 |
| 9.447 ± 0.2 |
| 12.398 ± 0.2 |
| 13.677 ± 0.2 |
| 17.171 ± 0.2 |
| 17.644 ± 0.2 |
| 18.985 ± 0.2 |
| 20.142 ± 0.2 |
| 21.118 ± 0.2 |
| 21.62 ± 0.2 |
| 22.199 ± 0.2 |
| 24.173 ± 0.2 |
| 24.915 ± 0.2 |
| 26.828 ± 0.2 |
| 28.682 ± 0.2 |
| 30.418 ± 0.2 |
| 31.46 ± 0.2. |

2. The Form B according to claim 1, wherein an DSC pattern has an endothermic peak at 109±2° C.; and/or wherein there is a weight loss of between 4% and 4.2% in a TGA pattern of the Form B.

* * * * *